(12) United States Patent
Hampton et al.

(10) Patent No.: US 10,493,298 B2
(45) Date of Patent: Dec. 3, 2019

(54) CAMERA SYSTEMS AND METHODS FOR USE IN ONE OR MORE AREAS IN A MEDICAL FACILITY

(71) Applicant: VARIAN MEDICAL SYSTEMS, INC., Palo Alto, CA (US)

(72) Inventors: Lisa A. Hampton, Sunnyvale, CA (US); Jill Conrad, Redwood City, CA (US); Tanya Dempsey, Las Vegas, NV (US); Jenny Kuhelj, Toronto (CA); Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 130 days.

(21) Appl. No.: 14/450,050

(22) Filed: Aug. 1, 2014

(65) Prior Publication Data

US 2015/0035942 A1 Feb. 5, 2015

Related U.S. Application Data

(60) Provisional application No. 61/861,963, filed on Aug. 2, 2013.

(51) Int. Cl.
*G06T 19/00* (2011.01)
*A61N 5/00* (2006.01)
*A61N 5/10* (2006.01)

(52) U.S. Cl.
CPC ............ *A61N 5/1049* (2013.01); *G06T 19/00* (2013.01); *A61N 2005/1059* (2013.01); *G06T 2210/21* (2013.01)

(58) Field of Classification Search
CPC ................ G06T 19/00; G06T 2210/21; A61N 2005/1059; A61N 5/1049

USPC .......................................................... 348/42
See application file for complete search history.

(56) References Cited

U.S. PATENT DOCUMENTS

| | | | |
|---|---|---|---|
| 6,246,900 B1 * | 6/2001 | Cosman ................. | A61B 90/10 600/426 |
| 6,272,368 B1 | 8/2001 | Alexandrescu | |
| 6,504,899 B2 | 1/2003 | Pugachev et al. | |
| 6,735,277 B2 | 5/2004 | McNutt et al. | |
| 7,245,698 B2 | 7/2007 | Pang et al. | |
| 7,268,358 B2 | 9/2007 | Ma et al. | |
| 7,529,339 B2 | 5/2009 | Goldman et al. | |
| 7,773,723 B2 | 8/2010 | Nord et al. | |
| 7,835,494 B2 | 11/2010 | Nord et al. | |
| 8,175,892 B2 | 5/2012 | Kapoor et al. | |

(Continued)

FOREIGN PATENT DOCUMENTS

| | | |
|---|---|---|
| CN | 200984237 Y | 12/2007 |
| DE | 10 2008 046 345 B4 | 7/2010 |

(Continued)

*Primary Examiner* — Zhihan Zhou
(74) *Attorney, Agent, or Firm* — Vista IP Law Group, LLP

(57) ABSTRACT

A method of monitoring an object during a medical process includes: using one or more cameras to obtain information regarding an actual three dimensional configuration of an object involved in a medical process; obtaining a three-dimensional model of the object representing a geometry of the object; obtaining a movement model of the object; and processing the information, the three-dimensional model, and the movement model to monitor the object during the medical process, wherein the act of processing is performed using a processing unit.

39 Claims, 19 Drawing Sheets

(56) References Cited

U.S. PATENT DOCUMENTS

| | | |
|---|---|---|
| 8,986,186 B2 | 3/2015 | Zhang et al. |
| 9,211,423 B2 | 12/2015 | Gross et al. |
| 2004/0034302 A1* | 2/2004 | Abovitz .................. A61B 90/36 600/428 |
| 2004/0042582 A1* | 3/2004 | Ein-Gal ............... A61N 5/1049 378/8 |
| 2004/0042583 A1 | 3/2004 | Wackerle et al. |
| 2005/0018069 A1* | 1/2005 | Krogmann ............. G02B 13/06 348/340 |
| 2006/0079757 A1* | 4/2006 | Smith ................... A61N 5/1049 600/416 |
| 2007/0016014 A1* | 1/2007 | Hara ........................ A61N 5/10 600/426 |
| 2008/0170123 A1* | 7/2008 | Albertson ........... A63B 24/0003 348/157 |
| 2009/0175406 A1* | 7/2009 | Zhang ................... A61B 5/113 378/8 |
| 2009/0187112 A1* | 7/2009 | Meir ....................... A61B 5/113 600/534 |
| 2011/0249088 A1* | 10/2011 | Hannibal ............. A61N 5/1048 348/43 |
| 2012/0271094 A1 | 10/2012 | Fuller |
| 2012/0275686 A1* | 11/2012 | Wilson ............... G06K 9/00355 382/154 |
| 2013/0033700 A1* | 2/2013 | Hallil .................... G01B 11/00 356/72 |
| 2013/0083894 A1 | 4/2013 | Niebler et al. |
| 2013/0142310 A1 | 6/2013 | Fahimian et al. |
| 2014/0028854 A1* | 1/2014 | Heinke .................... H04N 5/33 348/164 |
| 2014/0042319 A1* | 2/2014 | Pickett ..................... H04N 5/33 250/330 |
| 2014/0299775 A1* | 10/2014 | Kimmel ............. G06K 9/00771 250/341.8 |
| 2014/0376790 A1 | 12/2014 | Mostafavi |
| 2015/0208999 A1 | 7/2015 | Steinfeld et al. |
| 2015/0324967 A1 | 11/2015 | Newell et al. |
| 2016/0161938 A1* | 6/2016 | Popple ............... G05B 19/4061 700/275 |

FOREIGN PATENT DOCUMENTS

| | | |
|---|---|---|
| DE | 10 2012 203 767 A1 | 7/2013 |
| JP | 2014-128352 | 7/2014 |
| WO | WO 2011/153639 A2 | 12/2011 |
| WO | WO 2015/017630 A1 | 2/2015 |
| WO | WO 2015/017639 A1 | 2/2015 |
| WO | WO 2016/014422 A1 | 1/2016 |

* cited by examiner

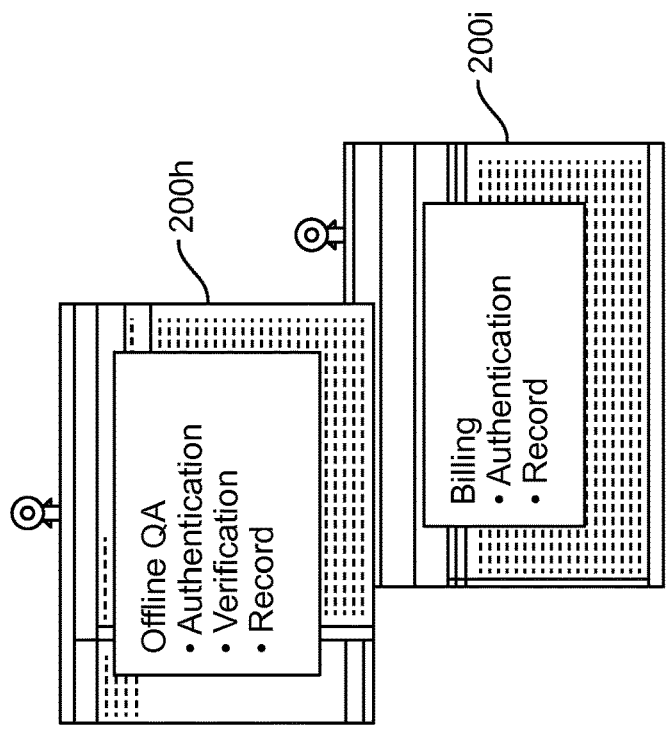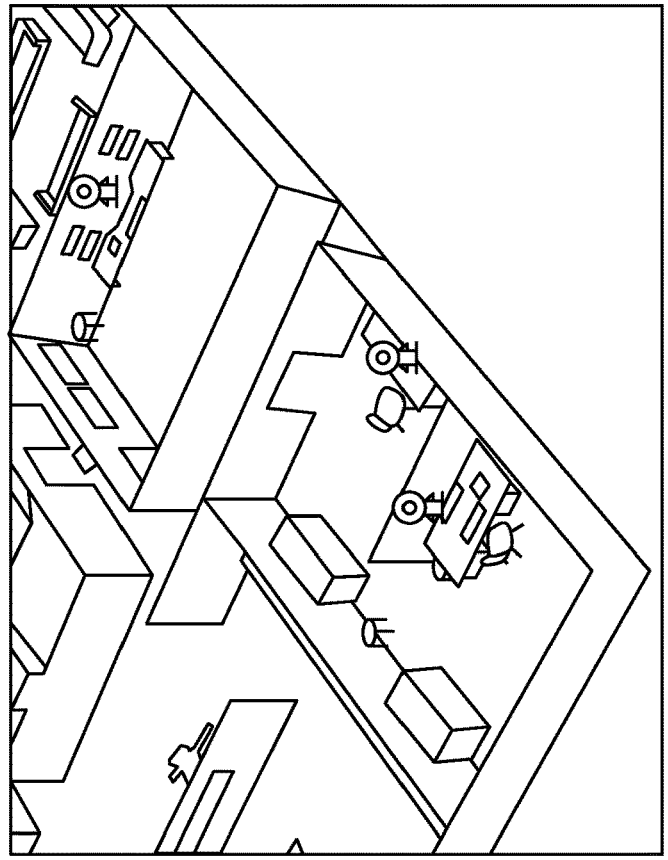
FIG. 2E

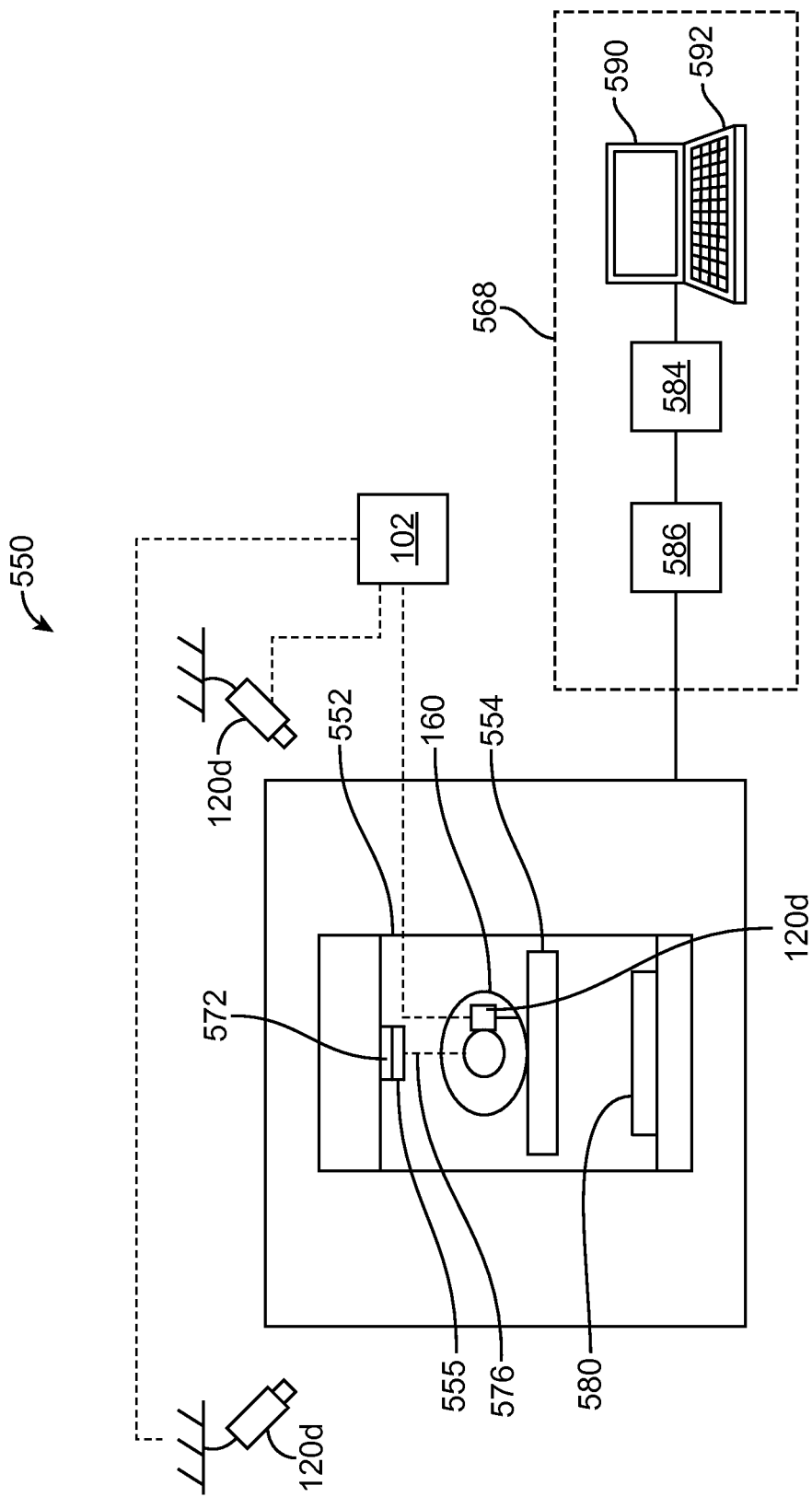

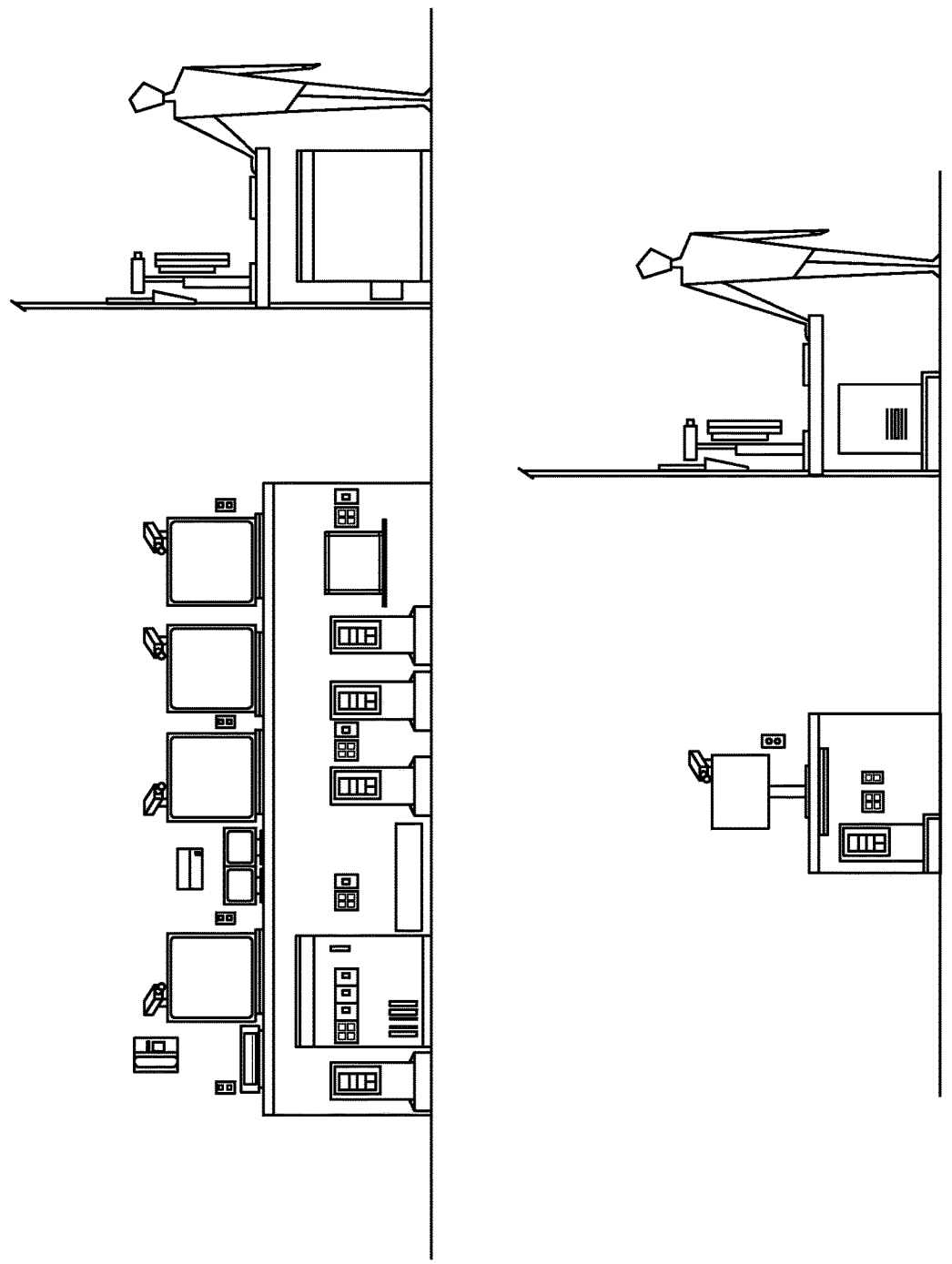

CAMERA SYSTEMS AND METHODS FOR USE IN ONE OR MORE AREAS IN A MEDICAL FACILITY

RELATED APPLICATION DATA

This application claims priority to and the benefit of U.S. Provisional Patent Application No. 61/861,963, filed on Aug. 2, 2013. The entire disclosure of the above application is expressly incorporated by reference herein.

FIELD

The field of the application relates to systems and methods for use in medical procedures, and more specifically, to camera systems and methods for use in medical procedures.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. During radiation therapy, a radiation source may be rotated around a patient to deliver radiation from different angles to a target region inside the patient. The radiation source may be mounted on an arm or a ring gantry. In certain radiation therapy, the patient support system may also move. Despite careful treatment planning, during a medical procedure, a collision may occur between a moving part of a medical device and a patient. For example, the gantry of the radiation therapy machine and the patient may possibly collide during radiation therapy treatment. As the dose delivery plans become more complex, the combination of a rotating gantry during treatment and imaging; and couch movement for non-coplanar beam delivery has increased the chance of potential collisions.

Also, in some cases, it may be desirable to monitor a patient's movement (such as breathing, twitching and relaxation) during a radiation therapy treatment. For example, a patient's breathing state or patient motion, due to relaxation, may shift the position of the target. may be used to gate the delivery of the radiation beam There are existing products for performing specific functions during a radiation therapy treatment. For example, there are products for monitoring collisions, monitoring patients, and determining movement and breathing, respectively. Bar-coding, biometrics, and RFID are used for patient and user identification, user rights authentication, tracking, and device and accessory verification. Software algorithms that support collision detection and avoidance may be built into some linear accelerators. Also, there are existing technologies for distance measurement, code reading, three-dimensional digital image rendering, three-dimensional device modeling, robotic motion management, providing context sensitive responses, recording patient history, providing image records, auditing user actions and tasks, respectively.

In the current state of technology, in order to achieve some or all of the above functionalities, multiple technologies, systems, applications, hardware and software are required. These multiple technologies, systems, applications, hardware and software may be developed by different companies, and are incompatible with each other. Also, these technologies would necessarily work independently or external to each other due to the targeted nature of the technology. As a result, user interaction would be different depending on the task to be performed or functionality to be achieved. This causes user confusion and device complexity in a mission critical environment which cannot accommodate this burden.

Applicant of the subject application determines that it may be desirable to have a new system or methodology for patient identification, patient authentication, authentication of user of medical device(s), object (device and/or person) verification, object tracking, patient data measuring, medical data interpreting, collision avoidance, recording and auditing of medical data (such as human action and motion, machine action and motion, equipment action and motion), and/or any combination of the foregoing, in a medical process, including but not limited to oncology evaluation, diagnosis, treatment planning, treatment simulation, treatment, and follow-up process.

SUMMARY

A. Object Monitoring During Diagnostic Imaging Procedures, Treatment Planning, Simulation, and Treatment Delivery.

A method of monitoring an object during a medical process includes: using one or more cameras to obtain information regarding an actual three dimensional configuration of an object involved in a medical process; obtaining a three-dimensional model of the object representing a geometry of the object; obtaining a movement model of the object; and processing the information, the three-dimensional model, and the movement model to monitor the object during the medical process, wherein the act of processing is performed using a processing unit.

Optionally, the one or more cameras comprise only one camera.

Optionally, the one or more cameras comprise a depth sensing camera.

Optionally, the one or more cameras comprise a plurality of cameras, and the information comprises a three-dimensional rendering of the object obtained using images from the cameras.

Optionally, the act of processing comprises creating an expected three-dimensional configuration of the object for a given time using the three-dimensional model and the movement model of the object.

Optionally, the act of processing further comprises comparing the expected three-dimensional configuration of the object with a three-dimensional rendering of the object obtained using images from the one or more cameras.

Optionally, the movement model indicates a degree of freedom, a trajectory, or both, for the object.

Optionally, the object comprises at least a component of a treatment machine.

Optionally, the object comprises at least a component of an imaging device.

Optionally, the object comprises at least a portion of a radiation machine.

Optionally, the object comprises at least a portion of a patient support system.

Optionally, the object is monitored to determine if there is a possible collision between the object and a patient.

Optionally, the object is monitored to determine if there is a possible collision between the object and another object.

Optionally, the one or more cameras comprise one or more two-dimensional digital cameras, one or more three-dimensional digital cameras, one or more Google glasses, one or more Kinect cameras, one or more infrared cameras, or combination of the foregoing.

Optionally, the one or more cameras comprise a camera coupled to a linear accelerator, a radiation treatment machine, a radiation imaging device, or a patient support system.

Optionally, the one or more cameras comprise a plurality of cameras coupled to a linear accelerator, a radiation treatment machine, a radiation imaging device, a patient support system, or a combination of the foregoing.

Optionally, the one or more cameras are coupled to a motor for moving the one or more cameras.

Optionally, the one or more cameras are shielded from radiation in an imaging room, simulation room, or a treatment room.

Optionally, the one or more cameras are disposable.

Optionally, the method further includes using the one or more cameras to monitor a patient during the medical process.

Optionally, the method further includes recording images generated by the one or more cameras.

Optionally, the method further includes using at least one of the one or more cameras or another camera(s) to obtain one or more images during the medical process, and processing the one or more images to monitor a patient during the medical process.

Optionally, the method further includes storing the images in a non-transitory medium.

Optionally, the method further includes using at least one of the one or more cameras or another camera(s) to obtain one or more images during the medical process, and processing the one or more images to track multiple objects during the medical process.

Optionally, the multiple objects comprise two or more of: a patient, an imaging system, a patient support system, a machine accessory, an immobilization device, and a patient-specific device.

Optionally, the method further includes using at least one of the one or more cameras or another camera(s) to obtain one or more images during the medical process, and processing the one or more images to determine a spatial distance between two objects.

Optionally, the method further includes using at least one of the one or more cameras or another camera(s) to obtain one or more images during the medical process, and processing the one or more images to determine an object-to-isocenter distance.

Optionally, the method further includes using at least one of the one or more cameras or another camera(s) to obtain one or more images during the medical process, and processing the one or more images to determine a body shape and/or size of a patient.

Optionally, the method further includes using at least one of the one or more cameras or another camera(s) to obtain one or more images during the medical process, and processing the one or more images to determine a source-to-skin distance.

Optionally, the medical process comprises an imaging process.

Optionally, the medical process comprises a treatment planning process.

Optionally, the medical process comprises a simulation process.

Optionally, the medical process comprises a treatment delivery process.

A system for monitoring an object during a medical process includes: one or more cameras; a non-transitory medium storing a three-dimensional model of an object and a movement model of the object; and a processing unit configured to process images from the one or more cameras to obtain information regarding an actual three-dimensional configuration of the object, the three-dimensional model, and the movement model to monitor the object during the medical process.

Optionally, the one or more cameras comprise only one camera.

Optionally, the only one camera comprises a depth sensing camera.

Optionally, the one or more cameras comprise a plurality of cameras, and the information comprises a three-dimensional rendering of the object obtained using images from the cameras.

Optionally, the processing unit is configured to create an expected three-dimensional configuration of the object for a given time using the three-dimensional model and the movement model of the object.

Optionally, the processing unit is configured to compare the expected three-dimensional configuration of the object with a three-dimensional rendering of the object obtained using images from the one or more cameras.

Optionally, the movement model indicates a degree of freedom, a trajectory, or both, for the object.

Optionally, the object comprises at least a component of a treatment machine.

Optionally, the object comprises at least a component of an imaging device.

Optionally, the object comprises at least a portion of a radiation machine.

Optionally, the object comprises at least a portion of a patient support system.

Optionally, the processing unit is configured to monitor the object to determine if there is a possible collision between the object and a patient.

Optionally, the processing unit is configured to monitor the object to determine if there is a possible collision between the object and another object.

Optionally, the one or more cameras comprise one or more two-dimensional digital cameras, one or more three-dimensional digital cameras, one or more Google glasses, one or more Kinect cameras, one or more infrared cameras, or combination of the foregoing.

Optionally, the one or more cameras comprise a camera coupled to a linear accelerator, a radiation treatment machine, a radiation imaging device, or a patient support system.

Optionally, the one or more cameras comprise a plurality of cameras coupled to a linear accelerator, a radiation treatment machine, a radiation imaging device, a patient support system, or a combination of the foregoing.

Optionally, at least one of the one or more cameras is coupled to a motor and is moveable by the motor.

Optionally, the one or more cameras are coupled to a motor for moving the one or more cameras.

Optionally, the one or more cameras are shielded from radiation in an imaging room, simulation room, or a treatment room.

Optionally, the one or more cameras are disposable.

Optionally, the processing unit is configured to use the one or more cameras to monitor a patient during the medical process.

Optionally, the system further includes a database for storing images generated by the one or more cameras.

Optionally, the processing unit is further configured to process one or more images to monitor a patient during the medical process.

Optionally, the system further includes a non-transitory medium for storing the images.

Optionally, the processing unit is further configured to process one or more images to track multiple objects during the medical process.

Optionally, the multiple objects comprise two or more of a patient, an imaging system, a patient support system, a machine accessory, an immobilization device, and a patient-specific device.

Optionally, the processing unit is further configured to process one or more images to determine a spatial distance between two objects.

Optionally, the processing unit is further configured to process one or more images to determine an object-to-isocenter distance.

Optionally, the processing unit is further configured to process one or more images to determine a body shape and/or size of a patient.

Optionally, the processing unit is further configured to process the one or more images to determine a source-to-skin distance.

Optionally, the medical process comprises an imaging process.

Optionally, the medical process comprises a treatment planning process.

Optionally, the medical process comprises a simulation process.

Optionally, the medical process comprises a treatment delivery process.

A computer product includes a non-transitory medium storing a set of instructions, an execution of which causes a method of monitoring an object during a medical process to be performed, the method comprising: obtaining information regarding a three dimensional position of an object involved in a medical process from one or more cameras; obtaining a movement model of the object; and processing the information and the movement model to monitor the object during the medical process.

A system for use in a medical process includes: one or more cameras for providing one or more images; and a processing unit configured to receive the one or more images; wherein the processing unit is configured to process one or more images to monitor a patient during the medical process.

A system for use in a medical process includes: one or more cameras for providing one or more images; and a processing unit configured to receive the one or more images; wherein the processing unit is configured to process one or more images to track multiple objects during the medical process.

Optionally, the multiple objects comprise two or more of: a patient, an imaging system, a patient support system, a machine accessory, an immobilization device, and a patient-specific device.

A system for use in a medical process includes: one or more cameras for providing one or more images; and a processing unit configured to receive the one or more images; wherein the processing unit is configured to process one or more images to determine a spatial distance between two objects.

A system for use in a medical process includes: one or more cameras for providing one or more images; and a processing unit configured to receive the one or more images; wherein the processing unit is configured to process one or more images to determine an object-to-isocenter distance.

A system for use in a medical process includes: one or more cameras for providing one or more images; and a processing unit configured to receive the one or more images; wherein the processing unit is configured to process one or more images to determine a body shape and/or size of a patient.

A system for use in a medical process includes: one or more cameras for providing one or more images; and a processing unit configured to receive the one or more images; wherein the processing unit is configured to process the one or more images to determine a source-to-skin distance.

Optionally, the medical process comprises an imaging process.

Optionally, the medical process comprises a treatment process.

Optionally, the medical process comprises a treatment planning process.

Optionally, the medical process comprises a simulation process to simulate a treatment condition.

B. Patient and Machine Setup.

A setup method for a medical process, includes: using one or more cameras to obtain image data of an object involved in a medical process; obtaining identity information associated with a setup criterion for the medical process; processing the image data to determine whether the setup criterion is met, wherein the act of processing is performed using a processing unit; and generating a signal based at least in part on a result of the act of processing.

Optionally, the identity information comprises an identity of a patient.

Optionally, the object comprises the patient, and the image data comprises image data of the patient.

Optionally, the act of processing comprises performing feature recognition to determine whether the patient in the image data has an identity that matches with the identity information associated with the setup criterion.

Optionally, the act of processing comprises displaying the image data together with a reference image of the patient.

Optionally, the identity information further comprises an identity of a medical device component.

Optionally, the identity of the medical device component comprises an identity of a patient immobilization device, an identity of a cone, or an identity of a filter.

Optionally, the object comprises the medical device component, and the image data comprises image data of the medical device component.

Optionally, the act of processing comprises performing feature recognition to determine whether the medical device component in the image data has an identity that matches with the identity information associated with the setup criterion.

Optionally, the act of processing comprises displaying the image data together with a reference image of the medical device component.

Optionally, the one or more cameras comprise one or more two-dimensional digital cameras, one or more three-dimensional digital cameras, one or more Google glasses, one or more Kinect cameras, one or more infrared cameras, or combination of the foregoing.

Optionally, the one or more cameras comprises a camera coupled to a linear accelerator, a radiation treatment machine, a radiation imaging device, or a patient support system.

Optionally, the one or more cameras comprises a plurality of cameras coupled to a linear accelerator, a radiation treatment machine, a radiation imaging device, a patient support system, or a combination of the foregoing.

Optionally, at least one of the one or more cameras is coupled to a motor and is moveable by the motor.

Optionally, the method further includes using at least one of the one or more cameras or another camera(s) to obtain one or more images during the medical process, and processing the one or more images obtained during the medical process to determine if there is a possible collision that is about to happen.

Optionally, the possible collision is between a radiation machine and a patient. By means of non-limiting examples, the radiation machine may be a radiation therapy machine, a simulation machine, and/or an imaging machine.

Optionally, the possible collision is between a radiation machine and a patient support system.

Optionally, the possible collision is between a radiation machine and another device. By means of non-limiting examples, the other device may be a patient immobilization device, IV poles, resuscitation cart, gurney, an imaging system, a ventilator, an anesthesia cart, a position sensing device (e.g., position sensing cart), a bolus device, a shield, any patient mounted beam modifier, any external device that is not a part of an imaging machine, treatment machine, and/or simulator, but is next to the machine/simulator, etc. In some embodiments, the radiation machine includes an on-board imager (OBI).

Optionally, the method further includes using at least one of the one or more cameras or another camera(s) to obtain one or more images during the medical process, and processing the one or more images to monitor a patient during the medical process.

Optionally, the method further includes storing the images in a non-transitory medium.

Optionally, the method further includes using at least one of the one or more cameras or another camera(s) to obtain one or more images during the medical process, and processing the one or more images to track multiple objects during the medical process.

Optionally, the multiple objects comprise two or more of a patient, an imaging system, a patient support system, a machine accessory, an immobilization device, and a patient-specific device.

Optionally, the method further includes using at least one of the one or more cameras or another camera(s) to obtain one or more images during the medical process, and processing the one or more images to determine a spatial distance between two objects.

Optionally, the method further includes using at least one of the one or more cameras or another camera(s) to obtain one or more images during the medical process, and processing the one or more images to determine an object-to-isocenter distance.

Optionally, the method further includes using at least one of the one or more cameras or another camera(s) to obtain one or more images during the medical process, and processing the one or more images to determine a body shape and/or size of a patient.

Optionally, the method further includes using at least one of the one or more cameras or another camera(s) to obtain one or more images during the medical process, and processing the one or more images to determine a source-to-skin distance.

Optionally, the medical process comprises an imaging process.

Optionally, the medical process comprises a treatment process.

Optionally, the medical process comprises a treatment planning process.

Optionally, the medical process comprises a simulation process to simulate a treatment condition.

Optionally, the signal is generated to inform an operator.

Optionally, the signal is generated to allow an activation of a radiation machine.

A system for us in a medical process, includes: one or more cameras configured to obtain image data of an object involved in a medical process; and a processing unit configured for: obtaining identity information associated with a setup criterion for the medical process; processing the image data to determine whether the setup criterion is met; and generating a signal based at least in part on a result of the act of processing.

Optionally, the identity information comprises an identity of a patient.

Optionally, the object comprises the patient, and the image data comprises image data of the patient.

Optionally, the processing unit is configured to perform feature recognition to determine whether the patient in the image data has an identity that matches with the identity information associated with the setup criterion.

Optionally, the system further includes a display for displaying the image data together with a reference image of the patient.

Optionally, the identity information further comprises an identity of a medical device component.

Optionally, the identity information comprises an identity of a medical device component.

Optionally, the identity of the medical device component comprises an identity of a patient immobilization device, an identity of a cone, or an identity of a filter.

Optionally, the object comprises the medical device component, and the image data comprises image data of the medical device component.

Optionally, the processing unit is configured to perform feature recognition to determine whether the medical device component in the image data has an identity that matches with the identity information associated with the setup criterion.

Optionally, the system further includes a display for displaying the image data together with a reference image of the medical device component.

Optionally, the one or more cameras comprise one or more two-dimensional digital cameras, one or more three-dimensional digital cameras, one or more Google glasses, one or more Kinect cameras, one or more infrared cameras, or combination of the foregoing.

Optionally, the one or more cameras comprises a camera coupled to a linear accelerator, a radiation treatment machine, a radiation imaging device, or a patient support system.

Optionally, the one or more cameras comprises a plurality of cameras coupled to a linear accelerator, a radiation treatment machine, a radiation imaging device, a patient support system, or a combination of the foregoing.

Optionally, at least one of the one or more cameras is coupled to a motor and is moveable by the motor.

Optionally, the processing unit is further configured to process one or more images obtained during the medical process to determine if there is a possible collision that is about to happen.

Optionally, the possible collision is between a radiation machine and a patient.

Optionally, the possible collision is between a radiation machine and a patient support system.

Optionally, the possible collision is between a radiation machine and another device.

Optionally, the processing unit is further configured to process one or more images to monitor a patient during the medical process.

Optionally, the system further includes a non-transitory medium for storing the images.

Optionally, the processing unit is further configured to process one or more images to track multiple objects during the medical process.

Optionally, the multiple objects comprise two or more of a patient, an imaging system, a patient support system, a machine accessory, an immobilization device, and a patient-specific device.

Optionally, the processing unit is further configured to process one or more images to determine a spatial distance between two objects.

Optionally, the processing unit is further configured to process one or more images to determine an object-to-isocenter distance.

Optionally, the processing unit is further configured to process one or more images to determine a body shape and/or size of a patient.

Optionally, the processing unit is further configured to process the one or more images to determine a source-to-skin distance.

Optionally, the medical process comprises an imaging process.

Optionally, the medical process comprises a treatment process.

Optionally, the medical process comprises a treatment planning process.

Optionally, the medical process comprises a simulation process to simulate a treatment condition.

Optionally, the signal is for informing an operator.

Optionally, the signal is for allowing an activation of a radiation machine.

A computer product includes a non-transitory medium storing a set of instructions, an execution of which causes a setup method for a medical process to be performed, the method comprising: obtaining image data of an object involved in a medical process from one or more cameras; obtaining identity information associated with a setup criterion for the medical process; processing the image data to determine whether the setup criterion is met, wherein the act of processing is performed using a processing unit; and generating a signal based at least in part on a result of the act of processing.

C. Launching Patient Chart, Treatment Plan, Treatment Session, Programs at Workstation Based on Images.

A system for use in a medical facility, includes: one or more cameras for providing one or more images of a patient; and a processing unit configured to receive the one or more images; wherein the processing unit is configured to process the one or more images to perform an identification check on the patient, and automatically launch an electronic patient chart for the patient based at least in part on a result of the identification check.

Optionally, the one or more cameras are configured to capture an image of the patient when the patient leaves the medical facility, and the processing unit is configured to close the electronic chart for the patient.

Optionally, the system further includes a non-transitory medium for recording medical data generated while the patient is in the medical facility.

A system for use in a medical facility, includes: one or more cameras for providing one or more images of a patient; and a processing unit configured to receive the one or more images; wherein the processing unit is configured to process the one or more images to perform an identification check on the patient, and automatically retrieve a treatment plan or initiate a treatment session for the patient based at least in part on a result of the identification check.

Optionally, the one or more cameras are configured to capture an image of the patient when the patient leaves the medical facility, and the processing unit is configured to close the treatment plan or the treatment session for the patient.

Optionally, the system further includes a non-transitory medium for recording medical data generated while the patient is in the medical facility.

A system for use in a medical facility, includes: one or more cameras for capturing one or more images of a user at a workstation; and a processing unit configured to receive the one or more images; wherein the processing unit is configured to process the one or more images to perform an identification check on the user, automatically launch designated application at the workstation, and automatically log the user into the application.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 2E illustrates cameras implemented in physics office and/or billing office.

FIG. 4 illustrates a radiation system for providing treatment.

FIGS. 8A-8B illustrate cameras implemented in a treatment room in accordance with some embodiments.

DETAILED DESCRIPTION

Figure 1A:
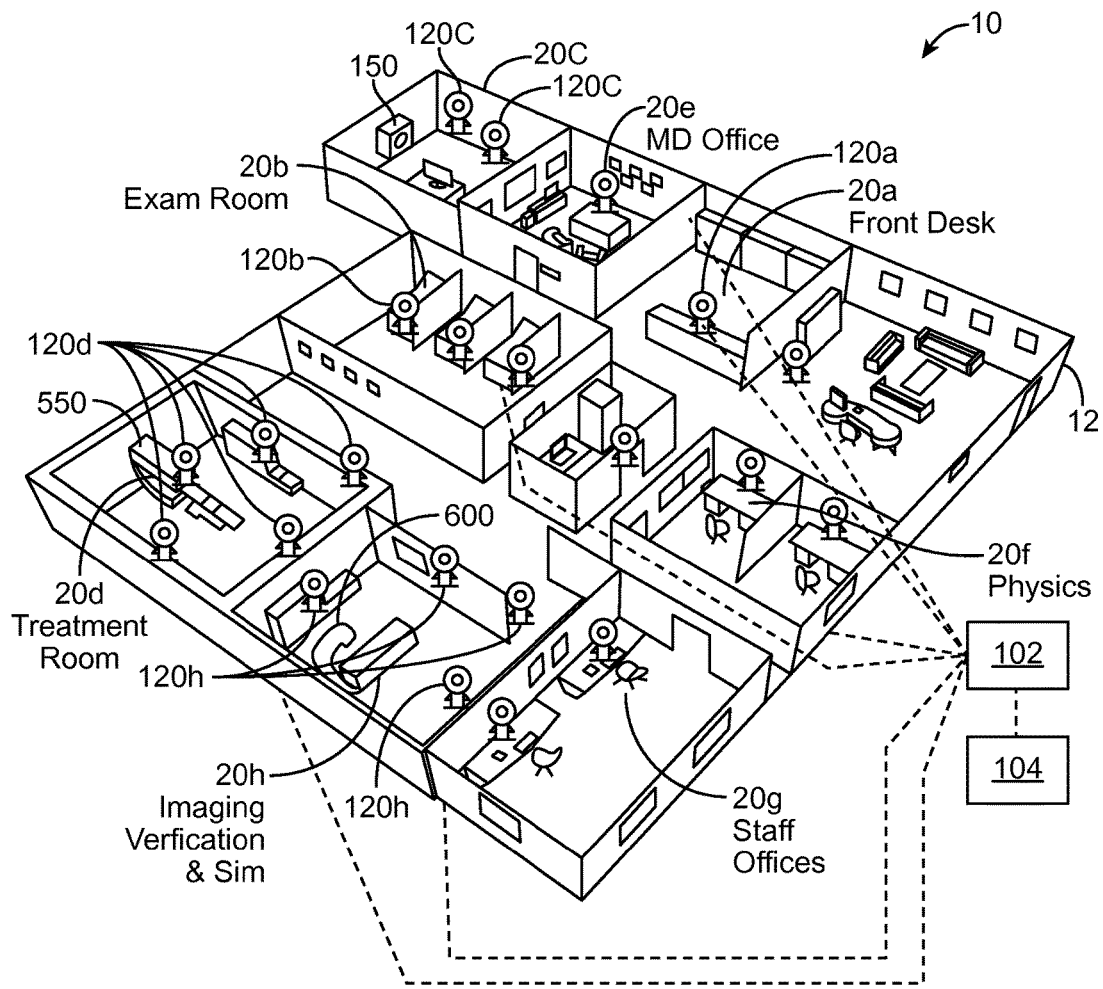
FIG. 1A illustrates a camera system implemented in a medical facility.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a camera system 10 implemented in a medical facility 12 in accordance with some embodiments. The medical facility 12 includes a front desk area 20a, an exam room 20b, an imaging room 20c, a simulation room 20h, and a treatment room 20d. The medical facility 12 also includes a MD office 20e, physics office(s) 20f, and staff office(s) 20g. In some embodiments, each of the areas/rooms 20a-20h may itself be considered a medical facility. Also, in some embodiments, the areas/rooms 20a-20h may be located at different buildings, different cities, etc.

The front desk area 20a is where a patient checks-in, and where a medical staff perform various administrative tasks for the patient.

The exam room 20b is where a patient is examined and where an operator enters and/or retrieves medical data for the patient (e.g., using a workstation, a computer, or a handheld device, such as an iPad, a tablet, a smart phone, etc.).

The imaging room 20c is where an imaging process is to be performed for the patient.

The simulation room 20h is where a simulation process is to be performed to simulate a treatment for a patient.

The treatment room 20d is where image-guided treatment delivery is performed, and where a patient is to be treated by a treatment machine.

The MD office 20e is the work area for doctor(s). The physics room(s) 20f is the work area for physicists, who provide consultation for operation of the radiation system. The staff office(s) 20g is the work area for the facility staffs.

As shown in the figure, the camera system 10 includes a plurality of cameras 120 implemented in the medical facility 12. The cameras 120 are communicatively coupled to a processing unit 102, which is configured to process the images captured by the cameras 120, and transmit them to a database 104 for storage of the images and information associated with the images. In some embodiments, the images captured by the cameras 120 may be transmitted from the processing unit 102, or from the cameras 120 directly, wirelessly to the database 104, e.g., through a Wi-Fi, for storage. In other embodiments, the images may be transmitted from the processing unit 102/cameras 120 through the Internet for storage in the database 104, as in a "Cloud". In further embodiments, the images may be transmitted through a cable to the database 104. Thus, the database 104 may be located in the same building in which the medical facility 12 is located, or may be located in other geographical location (e.g., in another building, another city, state, or country). Also, in some embodiments, the processing unit 102 and the database 104 may be integrated together, and/or may be located at the same geographical location. In some embodiments, the processing and temporary storage may be located in the treatment delivery room, a standard simulation room, or other location(s).

Although the processing unit 102 is illustrated in a block form in the figure, it should be understood that the processing unit 102 may have one or more components (e.g., processing module(s)), which may be at one or more workstations (which may be computer(s), or handheld device(s), such as iPad, tablet, iPhone, smartphone, any of other communication devices, etc.) in the facility 10, integrated at one or more devices (e.g., imaging system, treatment planning system, simulation system, treatment system, etc.) in the facility, at one or more location(s) in the facility 10, or any combination of the foregoing.

The camera(s) 120 in each of the areas/rooms 20 may be one or more two-dimensional digital camera(s), one or more three-dimensional digital camera(s), one or more Google glass(es), one or more Microsoft Kinect camera system(s), one or more infrared digital video camera(s), or any combination of the foregoing. Also, in some embodiments, one or more camera(s) 120 in one or more of the areas/rooms 20 may be one or more depth sensing camera(s). The depth sensing camera(s) may be infrared based, ultrasound based, or based on any of other time-of-flight techniques. Also, one or more camera(s) 120 in one or more of the areas/rooms 20 may have both visible image generation capability as well as infrared sensing capability.

In some embodiments, the processing unit 102 may be a processor, such as an ASIC processor, a FPGA processor, a general purpose processor, or any of other types of processor. Also, the processing unit 102 may include hardware, software, or combination of both. In further embodiments, the processing unit 102 may include multiple processors. For example, the camera in the front desk area 20a may be coupled to one processor of the processing unit 102, the cameras in the exam room 20b may be coupled to another processor of the processing unit 102, and the cameras in the treatment room may be coupled to another processor of the processing unit 102. One or more of the processors may be a part of a computer system, or a part of a handheld device, such as an iPad, a tablet, an iPhone, a smart phone, or any of other communication devices.

The database 104 may be one or more non-transitory media for storing data. In some embodiments, the database 104, or a part of it, may be implemented in one or more rooms 20 in the medical facility 10. For example, there may be a non-transitory medium (first component of the database 104) in the treatment room 20d, and another non-transitory medium (second component of the database 104) in the simulation room 20h, both of which are configured to store images and data obtained using the camera system 10. Also, in some embodiments, the database 104, or a part of it, may be one or more non-transitory media that are located remote from the medical facility 10. In further embodiments, the database 104, or a part of it, may be integrated with a medical device, such as an imaging system, a simulator, a treatment system, a positioning device, etc.

Figure 1B:
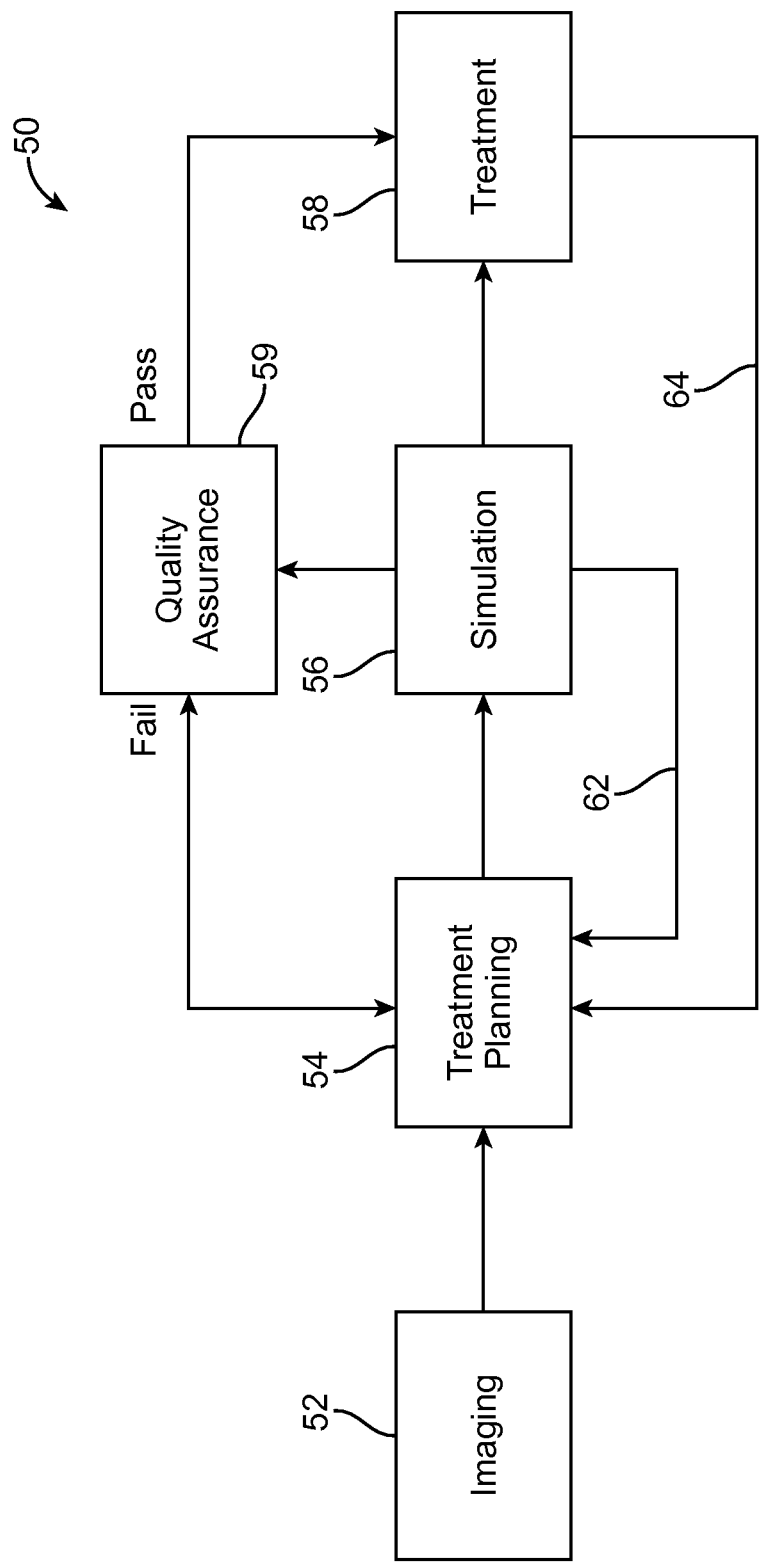
FIG. 1B illustrates a medical process that may be performed in the medical facility of FIG. 1A.

FIG. 1B illustrates a medical process 50 involving use of the camera system 10 that may be performed in the facility 10. First an imaging is performed for a patient (item 52). Such may be accomplished using any imaging equipment, such as CT machine, MRI device, x-ray device, ultrasound device, PET device, SPECT device, PET-CT device, etc. In some embodiments, the imaging of the patient may be performed in the imaging room 20c. During the imaging process 52, the camera(s) 120 of the camera system may capture camera images of the patient. The camera images may be processed by the processing unit 102, and/or may be stored in the database 104 for later processing.

Next, the medical images of the patient, as well as camera images captured by the camera(s) 120 (or any information derived from the camera image(s)) are input to a treatment planning system, which is used to perform treatment planning for the patient (item 54). The treatment planning may be performed at a workstation by a medical staff in the facility 10. In the illustrated embodiments, the treatment planning is performed before simulation process 56 and treatment 58 are performed. In other embodiments, the treatment planning may be performed after the simulation process 56 and/or after the treatment process 58 (as represented by loop-back arrows in the figure). For example, after the simulation process 56 and/or the treatment process 58, it may be decided that the treatment plan needs to be modified before further treatment is provided to the patient. In some embodiments, the treatment planning is performed after the patient goes home. In other embodiments, the treatment planning may be performed while the patient is in the imaging room 20c, in the simulation room 20h, or in the treatment room 20d.

As shown in FIG. 1B, after the treatment planning process 54, the simulation process 56 may be performed. The simulation process 56 may be performed in the simulation room 20h. During the simulation process 56, low radiation energy is delivered to the patient using a simulator that has similar configuration as the treatment system. This allows the medical staff to confirm that radiation will be delivered to the patient in a predictable and correct manner based on the treatment plan. In some embodiments, the simulation process 56 may be performed in a different day from the treatment process 58. In other embodiments, the simulation process 56 may be performed on the same day as the treatment process 58 (e.g., before treatment, and/or between deliveries of radiation during a treatment session).

In some embodiments, camera image(s) may be obtained using the camera(s) 120 of the camera system 10 during the simulation process 56. The camera image(s) and any information derived from it may then be later used in the treatment process 58, and/or during the treatment planning 54 (in a loop-back manner as represented by arrow 62).

After the simulation process 56 is performed, treatment may be provided to the patient (item 58). In the illustrated embodiments, the treatment process 58 may be performed in the treatment room 20d. In the treatment room 20d, a treatment system 550 is employed to deliver treatment radiation to treat the patient based on the treatment plan determined in item 54.

In some embodiments, camera image(s) may be obtained using the camera(s) 120 of the camera system 10 during the treatment process 58. The camera image(s) and any information derived from it may then be later used in the treatment planning 54 (in a loop-back manner as represented by arrow 64).

As shown in FIG. 1B, in some embodiments, a quality assurance process 59 may be performed before treatment process 58 is performed for the patient. This allows the treatment plan to be finalized and approved before treatment is provided to the patient. In some embodiments, if a result of the quality assurance process 59 indicates that further treatment planning and simulation are needed, the treatment planning process 54 and simulation process 56 may be repeated, until the quality assurance process 59 is passed. In some embodiments, the quality assurance process 59 may be implemented as a part of the simulation process 56. In other embodiments, the quality assurance process 59 may be implemented as a separate part of the simulation process 56.

Having described the overall process, details of the operation of the camera system 10 will now be described further.

In the illustrated embodiments, when a patient checks-in at the front desk area 20a, the camera 120a at the front desk area 20a captures an image of the patient, and transmits the image to the processing unit 102. If the visit is the patient's first visit to the office, the processing unit 102 then opens a new file for the patient, and stores the image of the patient in association with the new file, wherein the image will be used as a reference image for later processing. If the visit is a return visit by the patient, the processing unit 102 then accesses the database 104 to retrieve a reference image (e.g., photo) of the patient, and compares the image from the camera 120a with the reference image to confirm an identity of the patient. After the identity of the patient has been confirmed by the processing unit 102, the processing unit 102 then automatically launches the electronic patient file for the patient, and may transmit information in the file to a display for presentation to the medical staff. By means of non-limiting examples, the information in the electronic patient file may include one or a combination of a patient's name, a patient's address, a patient's contact information, a patient's social security number, medical insurance information, doctor's name and contact, and medical charges. Also, the display may be a computer screen, an iPad screen, a tablet screen, an iPhone screen, a smart phone screen, etc.

In some embodiments, before the medical staff at the front desk 20a is allowed access to the patient's electronic patient file, the camera 120a or another camera may be used to capture an image of the medical staff. The image may then be transmitted to the processing unit 102. The processing unit 102 then accesses the database 104 to retrieve a reference image (e.g., photo) of the medical staff, and compares the image from the camera with the reference image to confirm an identity of the medical staff. After the identity of the medical staff has been confirmed by the processing unit 102, the processing unit 102 then automatically launches any and all applications used by the medical staff. In some embodiments, the patients identity is confirmed when they enter a room and their electronic chart is opened for the medical staff to use. In some embodiments, the processing unit 102 may transmit information of the application and/or information in the file to a display for presentation to the medical staff. Also, in some embodiments, based on the identity of the user confirmed by the processing unit 102, the processing unit 102 may determine the associated rights of the user of the system for security and safety purposes. For example, if the user is a nurse, then the processing unit 102 may allow the user to perform nursing tasks, and may prevent the user from performing tasks that are reserved for doctors. If a user does not have the permission or associated rights for a task, the processing unit 102 then does not allow the action or task to be initiated or completed by the user.

After the electronic patient file has been launched, the medical staff may enter additional information to the patient file, and/or make changes to the existing information in the patient file.

Figure 2A:
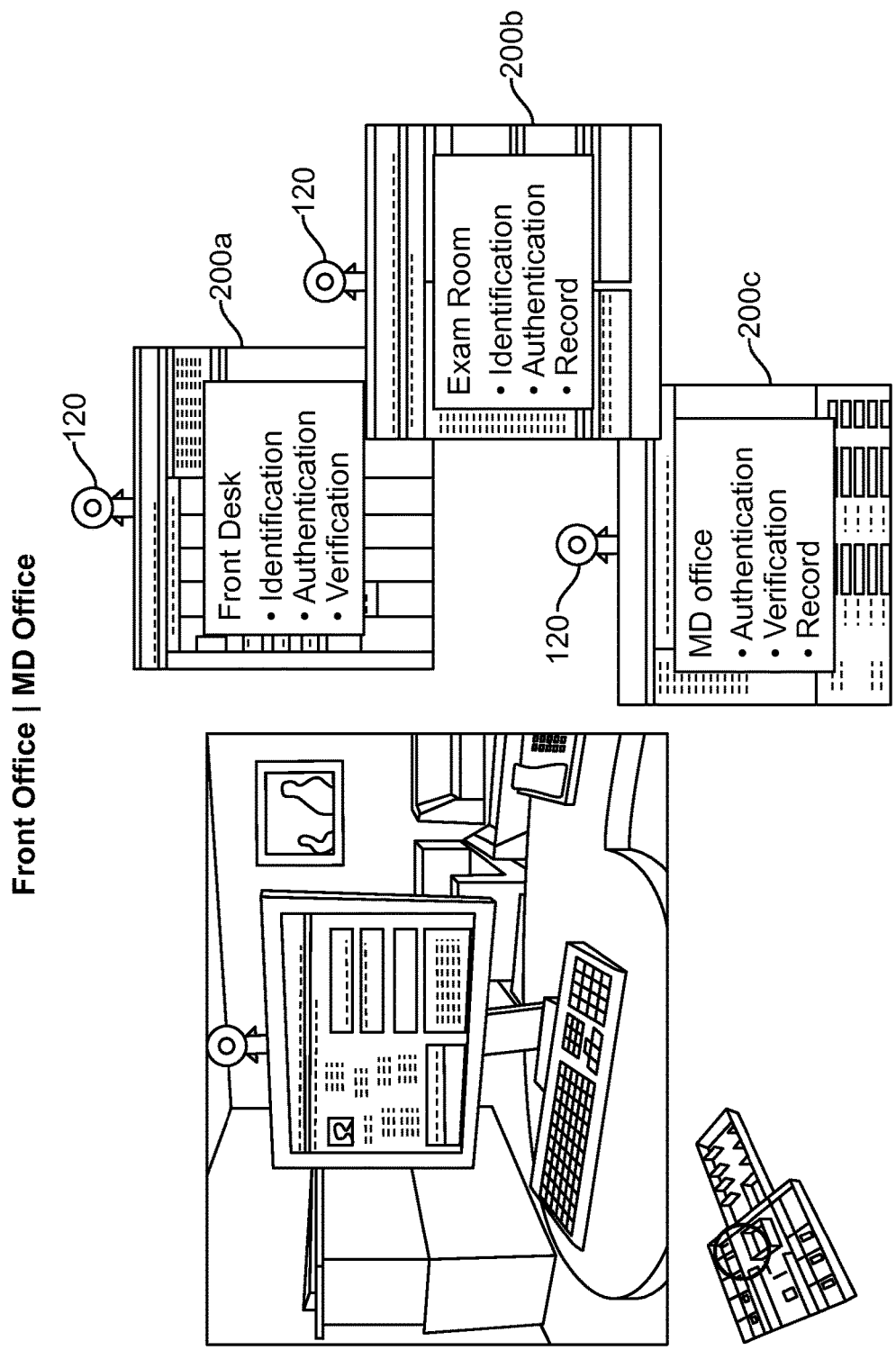
FIG. 2A illustrates a camera implemented at a work station for a front desk or a medical doctor's office.

FIG. 2A illustrates a user interface 200a with a camera, which may be implemented at the front desk 20a. The user interface may be implemented using a computer, an iPad, a tablet, an iPhone, a smart phone, or any of other handheld devices. As shown in the figure, at the front desk, the processing unit 102 may perform patient and/or user identification, patient and/or user authentication, and/or patient and/or user verification.

In some embodiments, when the patient leaves the front desk area 20*a*, the system 10 automatically captures an image of the patient (e.g., the face of the patient), closes the patient's electronic file, and records all changes.

After the patient has been checked-in for appointment at the front desk area 20*a*, the patient may then be directed to the exam room 20*b* and/or the MD office 20*e*.

At the examine room 20*b*, the camera 120*b* captures an image of the patient, and transmits the image to the processing unit 102. The processing unit 102 then accesses the database 104 to retrieve a reference image of the patient, and compares the image from the camera 120*b* with the reference image to confirm an identity of the patient. After the identity of the patient has been confirmed by the processing unit 102, the processing unit 102 then automatically launches the electronic patient file for the patient, and may transmit information in the file to a display for presentation to the medical staff at the exam room 20*b* and/or the MD office 20*e*. By means of non-limiting examples, the information in the electronic patient file may include one or a combination of a patient's name, a patient's address, a patient's contact information, a patient's social security number, medical insurance information, doctor's name and contact, and medical charges. The patient file may also include detail medical information, such as medical history, medical images (e.g., x-ray images, CT images, PET-CT images, ultrasound images, etc.), diagnosis, treatment plan, etc. Also, the display used by the medical staff in the exam room 20*b* may be a computer screen, an iPad screen, a tablet screen, an iPhone screen, a smart phone screen, etc.

At the examine room 20*b* and/or MD office 20*e*, the medical staff (e.g., a doctor, a nurse, etc.) may examine the patient and/or may ask the patient some medical questions. The medical staff may enter additional information to the patient file, and/or make changes to the existing information in the patient file.

In some embodiments, before the medical staff at the examine room 20*b*/MD office 20*e* is allowed access to the patient's electronic patient file, the camera 120 or another camera may be used to capture an image of the medical staff. The image may then be transmitted to the processing unit 102. The processing unit 102 then accesses the database 104 to retrieve a reference image (e.g., photo) of the medical staff, and compares the image from the camera with the reference image to confirm an identity of the medical staff. After the identity of the medical staff has been confirmed by the processing unit 102, the processing unit 102 then automatically launches the relevant application, and the electronic patient file of the patient for the medical staff, and may transmit information in the file to a display for presentation to the medical staff at the exam room 20*b*/MD office 20*e*. Also, in some embodiments, based on the identity of the user confirmed by the processing unit 102, the processing unit 102 may determine the associated rights of the user of the system for security and safety purposes. For example, if the user is a nurse, then the processing unit 102 may allow the user to perform nursing tasks, and may prevent the user from performing tasks that are reserved for doctors. If a user does not have the permission or associated rights for a task, the processing unit 102 then does not allow the action or task to be initiated or completed by the user.

Figure 2B:
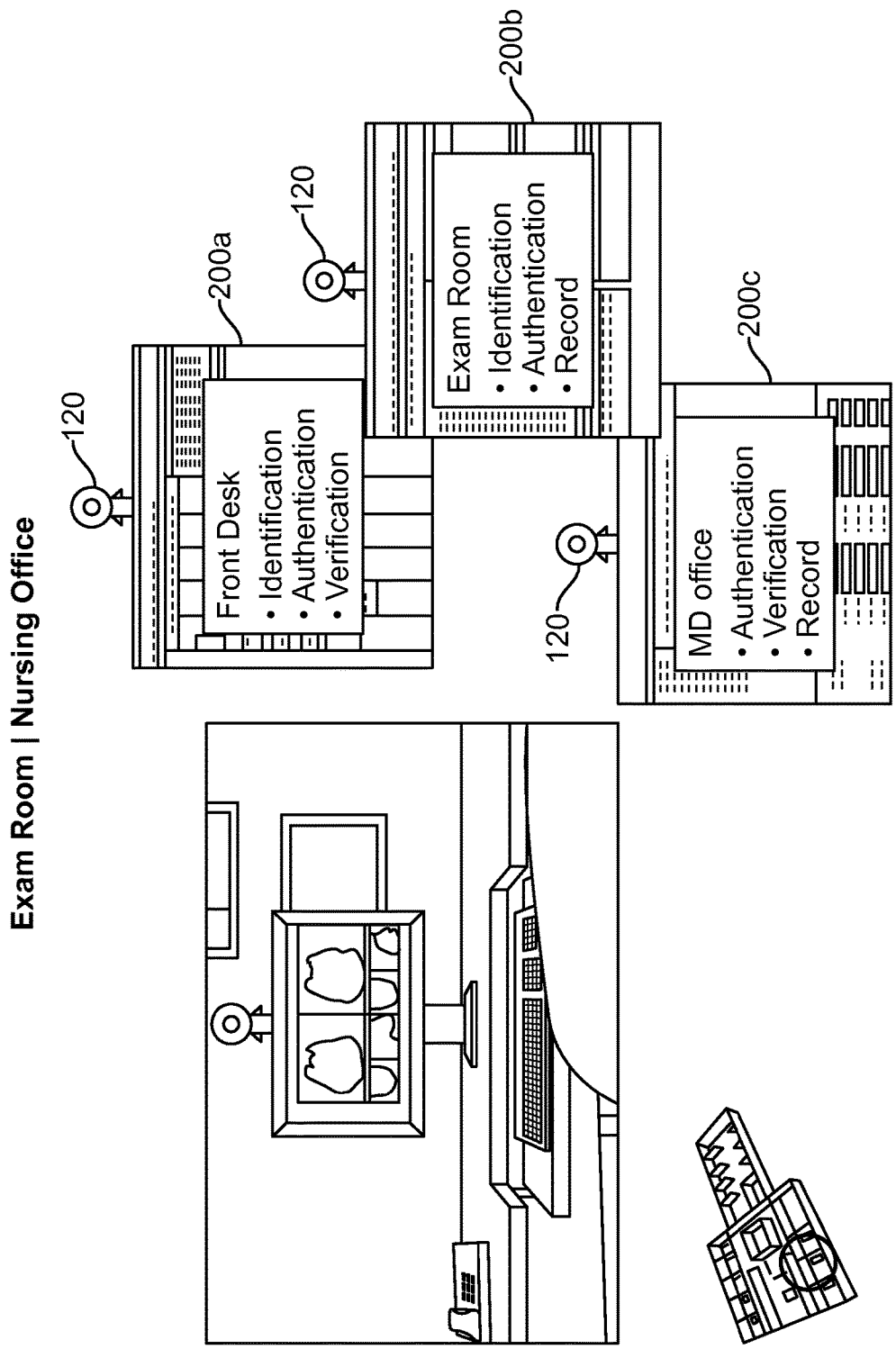
FIG. 2B illustrates a camera implemented at a work station for an exam room or a nursing office.

FIG. 2B illustrates a user interface 200*b*/200*c* with a camera, which may be implemented at the exam room 20*b* and/or the MD office 20*e*. The user interface may be implemented using a computer, an iPad, a tablet, an iPhone, a smart phone, or any of other handheld devices. As shown in the figure, at the exam room 20*b* and/or the MD office 20*e*, the processing unit 102 may perform patient and/or user identification, patient and/or user authentication, patient and/or user verification, recording of user actions and images (e.g., images of the patient), and/or automatic launching of programs.

In some embodiments, when the patient leaves the exam room 20*b*/MD office 20*e*, the system 10 automatically captures an image of the patient (e.g., the face of the patient), closes the patient's electronic file, and records all changes.

After the patient has been examined in the exam room 20*b* and/or the MD office 20*e*, the patient may then be directed to the imaging room 20*c*.

I. Imaging Operation

In the illustrated embodiments, the imaging room 20*c* has a radiation system 150 configured to perform an imaging process (like the imaging process 52 of FIG. 1B) to obtain medical images, and the medical images provided from the radiation system 150 may later be used for treatment planning, etc. In other embodiments, the imaging room 20*c* may include other types of treatment system 150, which may or may not involve delivery of radiation. As shown in FIG. 1, the imaging room 20*c* has a plurality of cameras 120*c* installed therein. The cameras 120*c* are configured to capture one or more images, and transmit the image(s) to the processing unit 102. The processing unit 102 is configured to process the image(s) to perform one or a plurality of tasks, such as patient identification confirmation, object (e.g., patient and device component(s)) verification, preventing collision between two objects, patient monitoring, object tracking, obtaining of operation data, and storing of data. Each of these tasks will be described in further detail below with reference to different types of operations, such as imaging operation, treatment planning, simulation operation, and treatment operation.

In some embodiments, the medical staff performing the imaging operation may be at a workstation that includes a camera 120, wherein the workstation is configured to operate the imaging radiation system. The workstation may be a computer station with a computer, or a handheld device, such as an iPad, a tablet, an iPhone, a smartphone, or any of other handheld devices. Before the medical staff at the station is allowed access to the patient's file and imaging software, the camera 120 or another camera may be used to capture an image of the medical staff. The image may then be transmitted to the processing unit 102. The processing unit 102 then accesses the database 104 to retrieve a reference image (e.g., photo) of the medical staff, and compares the image from the camera with the reference image to confirm an identity of the medical staff. After the identity of the medical staff has been confirmed by the processing unit 102, the processing unit 102 then automatically launches application. Once the patient has been identified, it launches the electronic patient file (which may include an imaging plan) for the medical staff, and may transmit information in the file to a display for presentation to the medical staff performing the imaging operation. Also, in some embodiments, based on the identity of the user confirmed by the processing unit 102, the processing unit 102 may determine the associated rights of the user of the system for security and safety purposes. For example, if the user is a nurse, then the processing unit 102 may allow the user to perform nursing tasks, and may prevent the user from performing tasks that are reserved for doctors. If a user does not have the permission or associated rights for a task, the processing unit 102 then does not allow the action or task to be initiated or completed by the user.

I-A. Patient Identity Confirmation

In some embodiments, when the patient is in the imaging room 20c, an imaging operation may be performed on the patient to image the patient using the radiation system 150. For example, the radiation system 150 may be a CT machine in some embodiments. In such cases, the patient is positioned on a patient support system 152. One or more cameras 120c in the room 20c then capture one or more images of the patient, and the image(s) is then transmitted to the processing unit 102 for identification of the patient. The processing unit 102 may access the database 104 to determine if there is a match between the image(s) captured by the camera(s) 120c with reference image(s) (e.g., photo(s)) stored in the database 104. If a match is found, then the processing unit 102 may identify the patient or confirm the identity of the patient based on the match. For example, if the matched reference image (photo) has the patient's name "Mary" associated therewith in the database 104, the processing unit 102 may then determine that the patient in the imaging room 20c is "Mary". In some embodiments, the process of patient identification performed by the processing unit 102 may involve feature extraction from the captured image(s), and image comparison between images. In one implementation, image comparison may be achieved by performing cross-correlation between the images. If the cross-correlation is above a prescribed threshold value (e.g., 0.7), then the processing unit 102 may determine that there is a match. In other embodiments, instead of performing image comparison using the processing unit 102, the processing unit 102 may transmit the captured image(s) and reference image(s) of the patient to a display for allowing a user (e.g., a medical staff) to verify the patient identity.

I-B. Auto-launching of Patient File

After the patient identity has been confirmed (either by the processing unit 102 or by the medical staff), the processing unit 102 may then automatically launch an electronic patient file for the medical staff while the patient is in the imaging room 20c. By means of non-limiting examples, the patient file may include the patient's medical chart, operation plan (e.g., treatment plan and/or imaging plan), and any of other information relating to the medical condition and treatment of the patient.

I-C. Component(s) Verification

In the illustrated embodiments, the operation to be performed on the patient is an imaging procedure. Before the imaging procedure is performed, a setup process may be performed to setup the imaging machine 150 and the patient. For example, a patient immobilization device (e.g., a head frame, a harness, a cuff, etc.) may be used to immobilize at least a portion of the patient. The immobilization device may have one or more features, such as an ID, a marking, etc., for identifying the immobilization device. In some embodiments, one or more cameras 120c in the imaging room 20c may capture image(s) of the immobilization device, and then transmit the image(s) to the processing unit 102. The processing unit 102 processes the image(s) to verify that the correct immobilization device is being used for the specific patient. For example, the processing unit 102 may perform feature extraction on the image(s) to identify the ID or marking on the immobilization device to determine an identity of the immobilization device. The processing unit 102 also obtains information (e.g., identity information) regarding the correct identity of the immobilization device from an operation plan (which may be included with the patient file accessed by the processing unit 102). The processing unit 102 then compares the identity of the immobilization device derived from processing of the image(s) captured by the camera(s) 120c with the identity of the device prescribed in the plan. If there is a match, then the processing unit 102 may determine that the correct immobilization device has been used, and that the setup concerning the immobilization device is correct.

It should be noted that the setup process may involve other medical components (which may be present on, or near, the system 150), which may or may not be patient-specific, and that the camera(s) 120c and the processing unit 102 may be employed to verify the identities of these components in a similar manner. For example, instead of, or in addition to, verifying the patient immobilization device, the camera(s) 120c may capture image(s) of other components, such as a collimating cone for attachment to the radiation machine, a filter for attachment to the radiation machine, the patient support system and associated accessories, an imager, a gantry (which may be a ring gantry, an arm gantry, or other types of gantry), IV poles, resuscitation cart, gurney, an imaging system, a ventilator, an anesthesia cart, a position sensing device (e.g., position sensing cart), a bolus device, a shield, any patient mounted beam modifier, etc. The image(s) are transmitted to the processing unit 102 for processing to determine the identity of the component(s). For example, the processing unit 102 may perform feature extraction (e.g., based on text recognition, shape recognition, color recognition, etc.) to determine the identity of the component(s). The processing unit 102 may also obtain the identity of the prescribed component(s) to be used in the operation from a plan that was stored in the database 104, and then compare the identity of the component(s) derived from the image(s) with the prescribed component(s)' identity. If the identity of the component(s) has been verified, then the processing unit 102 may determine that the correct component(s) has been used.

In some embodiments, after the processing unit 102 has verified an identity of the component(s) being used, the processing unit 102 may generate a signal to indicate the result of the verification. For example, the processing unit 102 may generate an audio signal, a visual signal (which may be a light signal, or an image such as a graphic for display in a screen), or both, to inform the medical staff that the correct component(s) is being used. On the other hand, if the processing unit 102 is unable to verify any of the components being used, then the processing unit 102 may generate a signal to prevent the imaging system 150 from being operated to deliver imaging radiation. Alternatively, or additionally, the processing unit 102 may generate a signal, such as an audio signal, a visual signal, or both, to inform the medical staff that the verification cannot be performed. In such medical staff may then conduct further investigation to ensure that the correct component(s) is being used, an may manually confirm the component(s).

In some embodiments, in the alternative to, or in addition to, using the processing unit 102 to verify the component(s), image(s) of the component(s) captured by the camera(s) 120c may be displayed together with reference image(s) of the prescribed component(s) retrieved from the database 104 in a screen. The screen may be a computer screen, an iPad screen, a tablet screen, an iPhone screen, a smartphone screen, etc. This allows the medical staff to determine whether the correct component(s) is being used, or to verify the verification result provided by the processing unit 102.

In some embodiments, the processing unit 102 is configured to not allow the radiation system 150 to be operated until all prescribed components have been identified and confirmed.

It should be noted that the camera(s) 120c for use to verify component(s) may be the same camera(s) as, or different camera(s) from, the camera(s) for use to verify patient identity. In other embodiments, the camera(s) 120c for verifying component(s) may be a subset or a superset of the camera(s) for verifying patient identity.

I-D. Collision Avoidance

After the component(s) for use in the medical process has been verified, the radiation machine 150 may then be activated to perform the imaging process. In the illustrated example, the medical process is an imaging process, and the radiation machine 150 in the imaging room 20c is a CT machine. However, it should be understood that in other embodiments, the imaging device 150 may be any imaging device, such as a MRI device, a x-ray device, an ultrasound device, a PET device, a SPECT device, a PET-CT device, etc.

Figure 3:
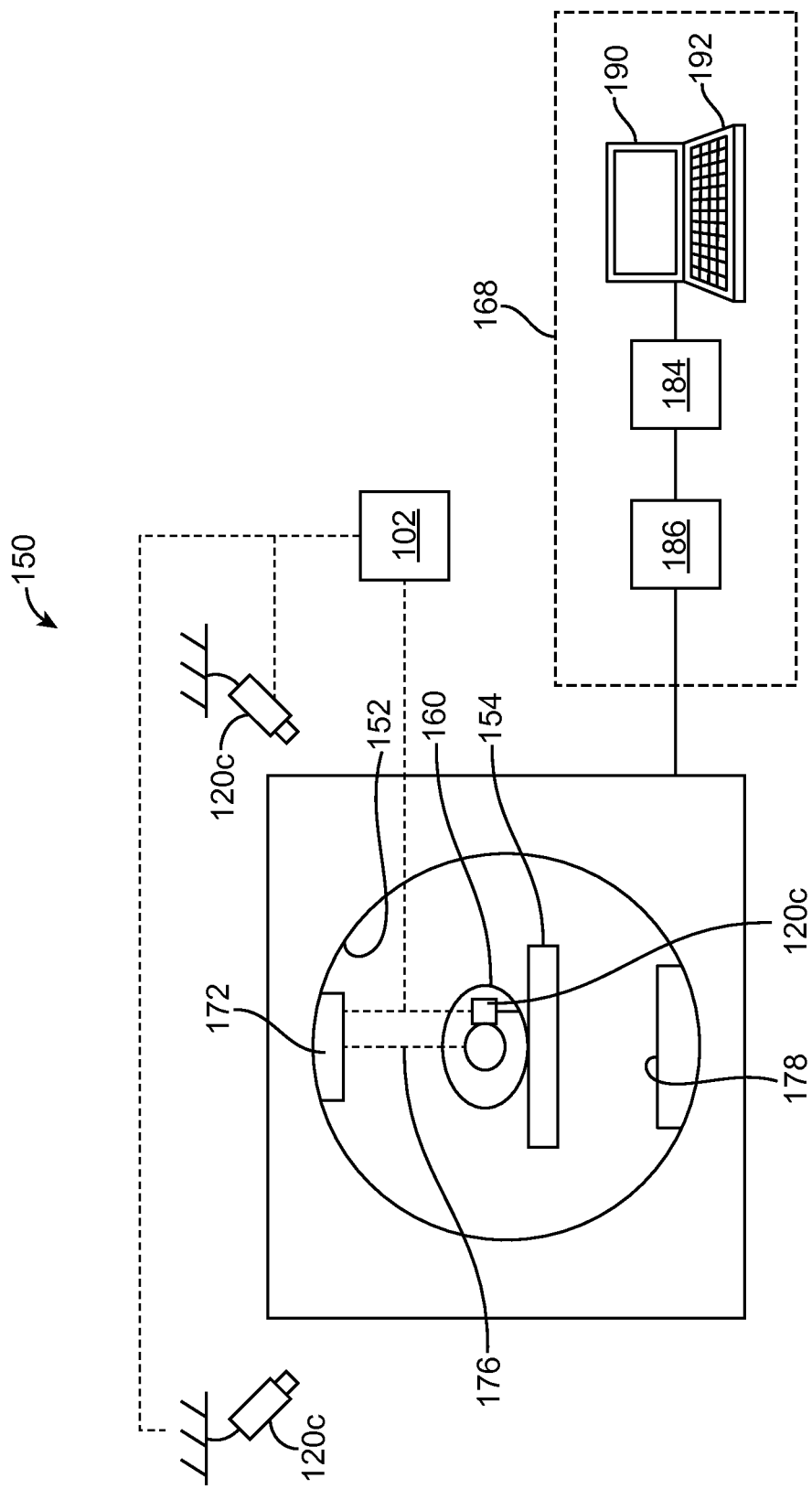
FIG. 3 illustrates a radiation system for providing images.

FIG. 3 illustrates an example of a radiation machine (or system) 150 configured to generate CT image data. The radiation system 150 includes a ring gantry 152, a patient support system 154 for supporting a patient 160, and a control system 168 for controlling an operation of the gantry 152 and delivery of radiation. The system 150 also includes a radiation source 172 that projects a beam 176 of radiation towards the patient 160 while the patient 160 is supported on support 154. The radiation system 150 also includes an imager 178 configured to receive the radiation generated by the radiation source 172 after it has penetrated through the patient. The radiation source 172 may be configured to generate a cone beam, a fan beam, or other types of radiation beams in different embodiments. Also, in other embodiments, the system 150 may have other form and/or configuration. For example, in other embodiments, instead of a ring gantry 152, the system 150 may have an arm gantry 152.

In the illustrated embodiments, the radiation source 172 is a diagnostic radiation source for providing diagnostic energy. In other embodiments, in addition to being a diagnostic radiation source, the radiation source 172 can also be a treatment radiation source for providing treatment energy for treatment purpose. In further embodiments, the radiation source 172 may be a treatment radiation source for providing treatment energy, wherein the treatment energy may be used to obtain images. In such cases, in order to obtain imaging using treatment energies, the imager 178 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 172 is able to generate X-ray radiation at a plurality of photon energy levels within a range anywhere between approximately 10 keV and approximately 20 MeV. In the illustrated embodiments, the radiation source 172 is carried by a ring gantry 152. Alternatively, the radiation source 172 may carried by an arm gantry 152.

In the illustrated embodiments, the control system 168 includes a processing unit 184, such as a processor, coupled to a control 186. The control system 168 may also include a monitor 190 for displaying data and an input device 192, such as a keyboard or a mouse, for inputting data. The operation of the radiation source 172 and the gantry 152 are controlled by the control 186, which provides power and timing signals to the radiation source 172, and controls a rotational speed and position of the gantry 152, based on signals received from the processing unit 184. Although the control 186 is shown as a separate component from the gantry 152 and the processing unit 184, in alternative embodiments, the control 186 can be a part of the gantry 152 or the processing unit 184.

In the illustrated embodiments, the system 150 is configured to deliver diagnostic radiation beam towards the patient 160 at different gantry angles. During a CT imaging procedure, the source 172 rotates around the patient 160 and delivers diagnostic radiation beam from different gantry angles towards the patient 160. The radiation exits through the patient 160 and is received by the imager 178. The imager 178 generates image signals in response to the received radiation to generate projection data at the different gantry angles. The projection data may be stored in a non-transitory medium, and may be later processed to reconstruct a three-dimensional volumetric image.

As shown in the figure, the radiation system 150 may have multiple cameras 120c mounted thereto, or to positions that are next to the radiation system 150. It should be noted that the positions of the cameras 120c are exemplary, and that in other embodiments, the camera(s) 120c may be mounted at any location on the system 150 and/or in close proximity to it. Although the processing unit 102 is illustrated as a separate component from the radiation system 150, in other embodiments, the processing unit 102, or at least a part of it, may be integrated with the radiation system 150. For example, it may be a part of the control 168 (such as a part of the processing unit 184) in some embodiments.

In some embodiments, while the radiation source 172 is rotated around the patient 160, one or more cameras 120c in the imaging room 20c may capture images of the radiation system 150 and the patient 160, and transmit the images to the processing unit 102 for processing. The processing unit 102 processes the images to determine whether there may be a possible collision between two objects that may be happening. The possible collision between two objects may be a possible collision between a component of the radiation system 150 and a person (e.g., the patient 160, a medical staff or personnel, etc.), a component (e.g., gantry 152, source 172, or imager 178) of the radiation system 150 and another component (patient support system 154) of the radiation system 150, or a component of the radiation system 150 and an external device/accessory/proximate device (e.g., a patient immobilization device, IV poles, resuscitation cart, gurney, an imaging system, a ventilator, an anesthesia cart, a position sensing device (e.g., position sensing cart), a bolus device, a shield, any patient mounted beam modifier, any external device that is not a part of an imaging machine, treatment machine, and/or simulator, but is next to the machine/simulator, etc.).

Various techniques may be employed in different embodiments for detecting a possible collision using images captured by the cameras 120c. In some embodiments, at least two cameras 120c are used to capture respective images of the radiation system 150, the patient 160, and other object(s) from different angles. The processing unit 102 may be configured to create three-dimensional rendering of the radiation system 150, the patient 160, and other object(s) using the two-dimensional images from the cameras 120c.

The rendering may be analyzed by the processing unit 102 to determine if a distance between two objects is within a prescribed threshold. If the distance is within the prescribed threshold, the processing unit 102 may determine that a possible collision may be about to happen, and may generate a signal to indicate such possible collision. The signal may be a warning signal in the form of a visual signal, an audio signal, or both, for informing the medical staff. In addition, or in the alternative, the signal may stop an operation of the radiation system 150. In some embodiments, if the processing unit 102 of the system 10 predicts or detects a possible collision, it may generate a signal to slow down the speed of machine movement in a specified collision warning zone, with resumption of standard motion speed if the zone is cleared. Also, in some embodiments, if a pending collision is detected, the processing unit 102 may generate a signal to stop all motion and beam delivery. In one implementation, there may be a first threshold/criteria for slowing down an operation of the system 150, and a second threshold/criteria for stopping the operation of the system 150. For example, if a distance between two objects is within a first threshold distance, then the processing unit 102 may generate a signal to slow down the operation of the system 150. If the distance between the two objects is within a second threshold distance (which is less than the first threshold distance), then the processing unit 102 may generate a signal to stop the operation of the system 150.

In some embodiments, the three-dimensional rendering of the machine, imager, patient support system (e.g., third party couch top), machine accessories, and immobilization devices, patient specific beam modifying devices, the patient, and proximate equipment may be used by the processing unit 102 to identify and track positions of each entity, and monitor the machine motion trajectory for collision detection and avoidance.

In other embodiments, the processing unit 102 may also obtain three-dimensional model(s) and movement model(s) for tracking different objects in the room. The three-dimensional model represents a geometry (e.g., shape and/or size) of an object (e.g., device component, such as gantry, arm, imager, etc.). The movement model indicates degrees of freedom and/or movement trajectory for one or more objects in the imaging room 20c. The three-dimensional model(s) and/or movement model(s) may be generated/determined in a simulation procedure, a planning process, an imaging procedure, and/or a treatment procedure. Alternatively, the three-dimensional model (e.g., the model of the radiation system 150) may be obtained from the manufacturer of the radiation system 150, which has all the geometric data concerning the size and shape of the radiation system 150. The three-dimensional model(s) and movement model(s) may be stored as part of an operation plan that is accessed by the processing unit 102. In some cases, there may be different movement models for different components. For example, there may be a first movement model that indicates a movement trajectory or degrees of freedom for the radiation source 172, and a second movement model that indicates a movement trajectory or degrees of freedom for the patient support system 154.

In some embodiments, the movement models may be processed together with the three-dimensional models (e.g., three-dimensional models of the radiation source 172 and the patient support system 154), and the rendering resulted from processing of the camera images, to determine whether a possible collision may be about to happen. For example, based on the physical geometry (e.g., shape and/or size) of the radiation source 172 and the physical geometry (e.g., shape and/or size) of the patient support system 154 (obtained from the three-dimensional models), and based on the direction of movement of the radiation source 172 and/or the patient support system 154 (obtained from the movement models), the processing unit 102 can determine an "expected" image of the scene in the imaging room 20c, which shows the expected position of the source 172 and the expected position of the support system 154. The processing unit 102 may then compare the rendering (which represents the real-time configuration of the source 172 and the support system 154) resulted from processing of the real-time camera images with the expected image. If rendering does not match the expected image, this indicates that the behavior of the system 150 does not match the expected behavior (e.g., the position of the gantry/source does not match the expected position). In such cases, the processing unit 102 may generate a signal to stop the operation of the imaging system 150 to prevent any possible object collision. In some embodiments, the rendering (derived from the camera image(s)) may be superimposed over the expected image (derived from the three-dimensional model(s) and the movement model(s) to generate a composite image. The composite image may be presented in a screen for presentation to a user, so that the user can visualize in real-time what the actual configuration of the objects (e.g., components and/or patient) is, versus the expected configuration of the objects (e.g., components and/or patient).

In other embodiments, the one or more cameras 120c may be one or more depth sensing cameras, which may be used to sense distances measured from a reference location to points on a surface of an object, or to points on different surfaces of different objects. In such cases, the output from the depth sensing camera(s) 120c may be used to determine the shapes of different objects, and/or distances between different points on different objects from a reference location. The shapes of different objects and/or the distances may then be used to determine positions of objects and/or whether two objects are close enough to indicate that a possible collision may be about to happen.

In some embodiments, the depth sensing camera 120c may use structured light for depth measurement (e.g., a Kinect camera). In other embodiments, the depth sensing camera 120c may use time-of-flight method for depth measurement (e.g., Mesa SR4000, or the new Microsoft Kinect2 camera). In further embodiments, the depth sensing camera 120c may be any device that is capable of sensing depth using any known techniques. It should be noted that the term "camera", as used in this specification, may be any device, and should not be limited to a device that provides "image" signals. For example, in some embodiments, the depth sensing camera 120c may be configured to provide depth signals, which may or may not be considered image signals, regardless of whether such depth signals are displayed in image form or not. A depth signal may be any signal indicating a depth or distance, or any signal from with a depth or distance may be derived. By means of non-limiting examples, the signal may be an infrared signal, an ultrasound signal, etc.

Also, in some embodiments, the depth sensing camera 120c may be infrared-based, in which cases, the depth may be sensed by the camera 120c using infrared. In some embodiments, such depth sensing camera 120c may be configured to output infrared video images from which depth images are formed. In some embodiments, these infrared video images may have exactly the same field of view as the depth images. Thus, the infrared video images may be used together with the depth images to determine whether there is a possible collision.

Furthermore, in some embodiments, the depth sensing camera 120c may include an infrared emitter, a color sensor, and an infrared depth sensor. The infrared depth sensor is configured to sense depth based on infrared signals output by the infrared emitter. The color sensor is configured to sense visible image. The depth signals and the visible image may then be used together by the processing unit 102 to determine whether there may be a possible collision that may be about to happen.

Also, in further embodiments, a depth sensing camera 120c may be used to capture a reference depth image of the radiation system 150 and the patient 160. During the imaging process, the depth sensing camera 120c generates multiple depth images in real time, and each of the real time depth images is subtracted from the reference depth image, or vice versa, to obtain a difference image. Values in the difference image within a region of interest are then analyzed by the processing unit 102 to determine if any of the values exceeds a threshold level. If so, then the processing unit 102 may determine that there is a possible collision that may be happening. Techniques using image subtraction to determine a possible collision has been disclosed in U.S. patent application Ser. No. 13/926,912, filed on Jun. 25, 2013, the entire disclosure of which is expressly incorporated by reference herein.

In the illustrated embodiments, the processing unit 102 is configured to automatically detect a possible collision. In other embodiments, a user may also participate in determining whether there is a possible collision. For example, in some cases, a screen (e.g., a computer screen, an iPad screen, a tablet screen, an iPhone screen, a smart phone screen, or any of other handheld device screens) may be used to continuously display the real time images from camera(s) and/or images (e.g., images of a three-dimensional models, images of rendering, composite images, etc.) derived by the processing unit 102 during the procedure, so that the person operating the treatment procedure may view the images and identify possible collisions. In one or more embodiments, the depth image and the optical image may be superimposed/overlaid to obtain a composite image that shows both depth and visible image.

In some embodiments, the processing unit 102 of the system 10 may provide a user interface for display in a screen (e.g., a computer screen, an iPad screen, a tablet screen, an iPhone screen, a smart phone screen, or a screen of any handheld devices), wherein in the user interface, directional arrow(s) (or other indicator(s)) indicating machine motion(s) is presented over a real time display of the three-dimensional composite model or the real-time image. These overlays will allow the user to visualize the direction a moving part is planned to be moving. When a collision or collision warning zone is detected, the entities will be identified to the user by highlight on the real time display of the three-dimensional composite model or the real-time image.

In some embodiments, the images captured during the operation of the radiation system 150 may be stored in a non-transitory medium, such as the database 104. This allows the images to be reviewed later if necessary.

It should be noted that the camera(s) 120c for use to detect possible collision may be the same camera(s) as, or different camera(s) from, the camera(s) for verifying component(s) and/or for verifying patient identity. In other embodiments, the camera(s) 120c for detecting possible collision may be a subset or a superset of the camera(s) for verifying component(s) and/or for verifying patient identity.

I-E. Object(s) Monitoring and Tracking

In some embodiments, during operation of the radiation system 150, one or more cameras 120c in the imaging room 20c may capture images for monitoring and/or tracking object(s). For example, the captured images may include images of the patient. In such cases, the processing unit 102 receives the images, and processes the images to monitor the patient.

In some embodiments, the processing unit 102 may process the images to determine whether the patient has moved away from a desired position. For example, the patient may have shifted away from the desired position, but may still remain in a field of view of the camera(s). In another example, the patient may have moved completely away so that the patient is no longer in the field of view of the camera(s), in which cases, the processing unit 102 may be configured to detect absence of the patient. If the patient has moved away from a desired position, then the processing unit 102 may generate a signal to stop the operation of the radiation system 150, and/or a signal to inform the medical staff. Otherwise, the processing unit 102 may let the operation of the radiation system 150 continue.

Also, some embodiments, the processing unit 102 may process the images to confirm that the patient is in the operative position or next to (e.g., in front of) the imaging machine while radiation is being delivered (e.g., during beam-on operation). If the patient cannot be detected by the camera(s) and the processing unit 102, then the processing unit 102 may generate a signal to stop the operation of the radiation system 150, and/or a signal to inform the medical staff. Otherwise, the processing unit 102 may let the operation of the radiation system 150 continue.

In other embodiments, the processing unit 102 may process the images to determine whether there is patient movement or not. If the patient has moved, then the processing unit 102 may generate a signal to stop the operation of the radiation system 150, and/or a signal to inform the medical staff. Otherwise, the processing unit 102 may let the operation of the radiation system 150 continue.

In further embodiments, the processing unit 102 may process the images to determine physiological movement (e.g., breathing motion). For example, the processing unit 102 may process the images to determine breathing amplitudes and/or breathing phases of the patient during operation of the radiation system 150. The determined physiological movement may be used to gate an operation of the radiation system 150. For example, in some embodiments, the processing unit 102 may be configured to generate a signal for activating the radiation source when the breathing amplitude is within a prescribed amplitude range, or when a breathing phase is within a prescribed phase range. In other embodiments, the processing unit 102 may be configured to generate a signal for de-activating the radiation source when the breathing amplitude is within a prescribed amplitude range, or when a breathing phase is within a prescribed phase range. Also, in further embodiments, the processing unit 102 may be configured to generate a signal to move the radiation source 172 and/or the patient support system 154 based on the determined physiological movement.

In other embodiments, the images captured by the camera(s) 120c may include images of one or more medical device components. In such cases, the processing unit 102 receives the images, and processes the images to monitor the medical device component(s). For example, the processing unit 102 may determine the position of a medical device component (e.g., the radiation source 172, the patient support system 154, or the imager 178) based on an analysis of the images. In some cases, the determined position may be used to confirm an intended position of the medical device component, as similarly discussed. For example, in some embodiments, three-dimensional model of a component and a movement model of the component may allow the processing unit 102 to determine an "expected" image that shows the expected position of the component at a certain time. The real-time camera image(s) may be processed by the processing unit 102 to determine a rendering of the component that shows the three-dimensional configuration of the component in real time. The three-dimensional rendering may then be compared with the expected image to determine whether the component is at the intended position or not.

In some embodiments, the images captured during the operation of the radiation system 150 may be stored in a non-transitory medium, such as the database 104. This allows the images to be reviewed later if necessary.

It should be noted that the camera(s) 120c for monitoring and/or tracking object(s) may be the same camera(s) as, or different camera(s) from, the camera(s) for verifying component(s), for verifying patient identity, and/or for detecting possible collision. In other embodiments, the camera(s) 120c for monitoring and/or tracking object(s) may be a subset or a superset of the camera(s) for verifying component(s), for verifying patient identity, and/or for detecting possible collision.

I-F. Obtaining of Patient Data and Operation Data

In some embodiments, before, during, and/or after operation of the radiation system 150, one or more cameras 120c in the imaging room 20c may capture one or more images for obtaining operation data. For example, in some embodiments, the image(s) may be transmitted to the processing unit 102, which processes the image(s) to determine a patient shape. In other embodiments, the processing unit 102 may process the image(s) to determine patient habitus and size. In further embodiments, the processing unit 102 may process the image(s) to determine a source-to-skin distance. In other embodiments, the processing unit 102 may process the image(s) to determine object distance from isocenter (object-to-isocenter distance), wherein the object may be a component (such as a radiation source, an imager, etc.), or a part of a patient. In still further embodiments, the processing unit 102 may process the image(s) to determine distance between two objects. The two objects may be a component of a radiation system and a patient, two components of a radiation system, or a component of a radiation system and an external device/accessory.

In some embodiments, the patient data and/or operation data obtained using the camera system 10 may be processed by the processing unit 102 to determine whether a condition (e.g., patient size has changed, patient position has changed, etc.) has met to automatically trigger an imaging process, a simulation process, and/or a treatment planning process, during the treatment of the patient.

Various techniques may be employed to determine operation data and/or patient data using image(s) obtained from the camera(s) 120c. In some embodiments, two-dimensional images obtained by multiple cameras 120c from different angles may be processed to determine three-dimensional shapes of different objects. Then distance between the objects may be calculated. In other embodiments, a distance between two locations in a reference image may be predetermined (e.g., through a calibration process), and then an image from a camera 120c may be analyzed (using geometric principles and scaling) to determine a distance between two locations in the image. In still further embodiments, the one or more cameras 120c may be one or more depth sensing cameras, which may be used to sense distances measured from a reference location to points on a surface of an object, or to points on different surfaces of different objects. In such cases, the output from the depth sensing camera(s) 120c may be used to determine the shapes of different objects, and/or distances between different points on different objects from a reference location.

Thus, in some embodiments, a system for use in a medical process includes: one or more cameras for providing one or more images; and a processing unit configured to receive the one or more images; wherein the processing unit is configured to process one or more images to determine a body shape and/or size of a patient.

In other embodiments, a system for use in a medical process includes: one or more cameras for providing one or more images; and a processing unit configured to receive the one or more images; wherein the processing unit is configured to process the one or more images to determine a source-to-skin distance.

In further embodiments, a system for use in a medical process includes: one or more cameras for providing one or more images; and a processing unit configured to receive the one or more images; wherein the processing unit is configured to process one or more images to determine an object distance from isocenter.

In still further embodiments, a system for use in a medical process includes: one or more cameras for providing one or more images; and a processing unit configured to receive the one or more images; wherein the processing unit is configured to process one or more images to determine a spatial distance between two objects.

I-G. Record Data

In some embodiments, images obtained by the cameras 120c in the imaging room 20c may be stored in a non-transitory medium, such as the database 104. Also, actions taken, tasks completed, operations of the radiation system 150, and user interactions (with the radiation system 150, applications, and patient file) may be stored in the non-transitory medium.

In some embodiments, the camera system 10 may include a user interface for providing a playback feature so that a user of the camera system 10 may view the images on a screen. For example, the user interface may be provided on a screen of a computer, an iPad, a tablet, an iPhone, a smartphone, or any of other handheld devices, so that the user can view the images. The images may be transmitted from the database 104 to the device with the user interface through a network connection. In some embodiments, the user interface may display the images in a playback configuration so that the user can view the images in a video format. Also, the user interface may display information regarding actions taken, tasks completed, operations of the radiation system 150, and user interactions (with the radiation system 150, applications, and patient file), simultaneously with the images in the screen.

The playback feature may be used as documentation, observation, and/or review of the operation, and/or for treatment planning. The playback feature may allow clinicians to visualize all actions taken during the operation using the radiation system 150 for quality assurance purposes. Additionally, the data for the playback feature may be used for clinical trials, outcome predictions, and legal review.

In some embodiments, when the patient leaves the imaging room 20c, the system 10 automatically captures an image of the patient (e.g., the face of the patient), closes the patient's electronic file, and records all changes.

Figure 2C:
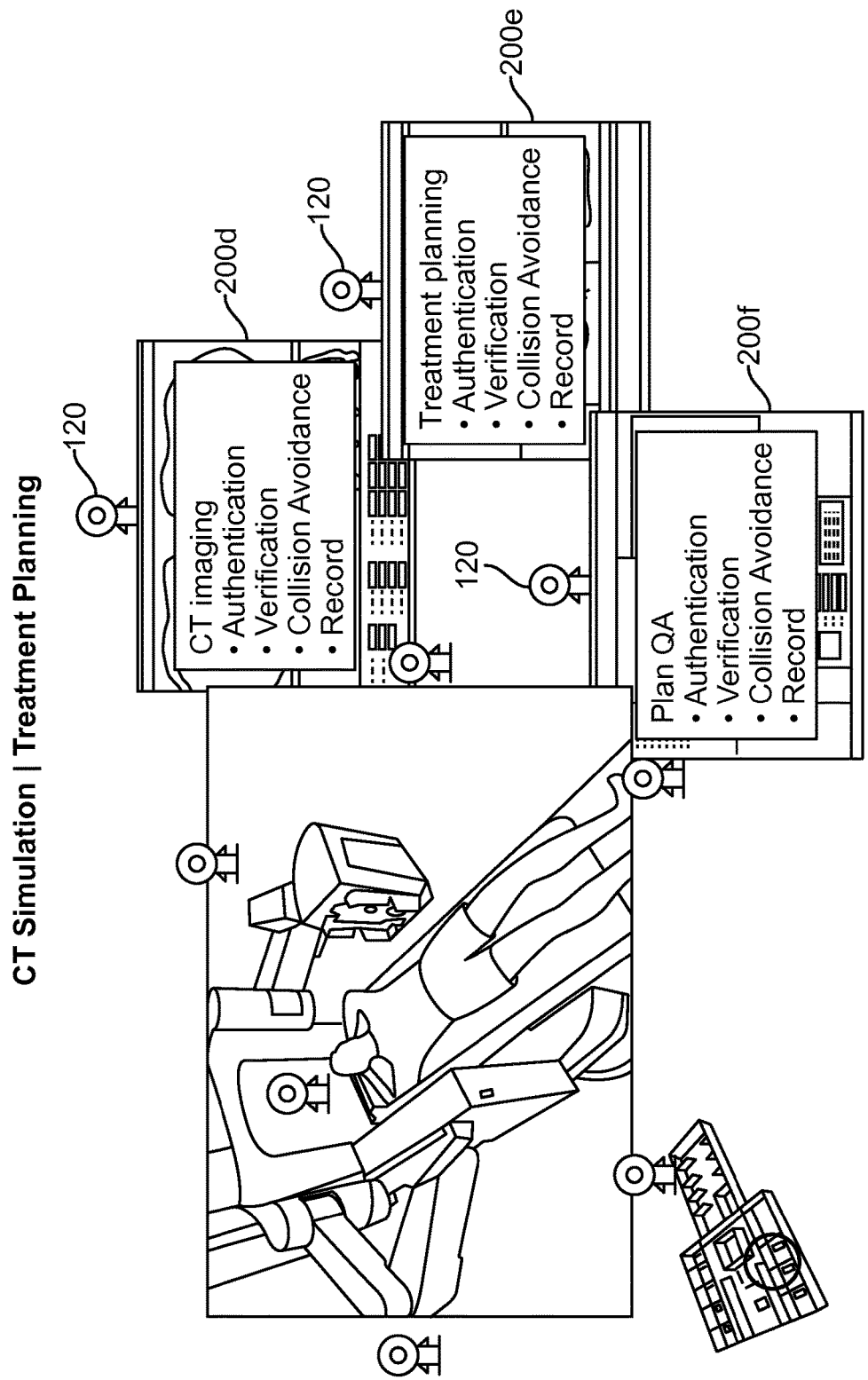
FIG. 2C illustrates cameras implemented at a medical device for imaging or treatment planning.

FIG. 2C illustrates a user interface 200d with a camera, which may be implemented at a station for operating an imaging device. The user interface may be implemented using a computer, an iPad, a tablet, an iPhone, a smart phone, or any of other handheld devices. As shown in the figure, the processing unit 102 for use during the imaging process may perform patient and/or user authentication, patient and/or user verification, components verification, collision avoidance, recording of user and/or patient actions and images, and/or automatic launching of programs.

II. Treatment Planning

In some embodiments, after the patient is imaged, a medical staff (e.g., in the staff office 20g) may perform a treatment planning (like the treatment planning 54 in FIG. 1B) to determine a treatment plan for the patient using the images generated during the imaging process.

In some embodiments, the medical staff performing the treatment planning may be at a workstation that includes a camera 120. The workstation may be a computer station with a computer, or a handheld device, such as an iPad, a tablet, an iPhone, a smartphone, or any of other handheld devices. Before the medical staff at the treatment planning station is allowed access to the patient's file and treatment planning software, the camera 120 or another camera may be used to capture an image of the medical staff. The image may then be transmitted to the processing unit 102. The processing unit 102 then accesses the database 104 to retrieve a reference image (e.g., photo) of the medical staff, and compares the image from the camera with the reference image to confirm an identity of the medical staff. After the identity of the medical staff has been confirmed by the processing unit 102, the processing unit 102 then automatically launches the relevant application. Also, after the identity of the patient is confirmed, the processing unit 102 automatically launches the electronic patient file of the patient for the medical staff, and may transmit information in the file to a display for presentation to the medical staff performing the treatment planning. Also, in some embodiments, based on the identity of the user confirmed by the processing unit 102, the processing unit 102 may determine the associated rights of the user of the system for security and safety purposes. For example, if the user is a nurse, then the processing unit 102 may allow the user to perform nursing tasks, and may prevent the user from performing tasks that are reserved for doctors. If a user does not have the permission or associated rights for a task, the processing unit 102 then does not allow the action or task to be initiated or completed by the user.

In some embodiments, the treatment planning may be performed after the patient has left the medical facility. In such cases, the medical staff performing the treatment planning may utilize images and data recorded during the imaging process to perform the treatment planning.

In other embodiments, the treatment planning may be performed while the patient is still in the medical facility. In such cases, additional information (e.g., images of the patient, motion data of the patient, images of the components, rendering of objects, etc.) may be collected with the assistance of the patient. For example, in some embodiments, the patient may remain in the imaging room 20c after the imaging process, or may be transported to the simulation room 20h or treatment room 20d, and a treatment planning may be performed while the patient is in one of these rooms.

While the patient is in a room 20 for treatment planning, the camera system 10 may be used to perform various functions, like those described previously.

For example, in some embodiments, the camera(s) 120 in the room 20 in which treatment planning is performed may be used to perform patient identity confirmation, like that described previously with reference to the imaging process performed in room 20c.

Also, the camera(s) 120 and the processing unit 102 may auto-launch a patient file for the purpose of treatment planning, like that described previously with reference to the imaging process performed in room 20c.

In addition, the camera(s) 120 and the processing unit 102 may perform component(s) verification during the treatment planning process, like that described previously with reference to the imaging process performed in room 20c.

Furthermore, the camera(s) 120 and the processing unit 102 may perform collision avoidance during the treatment planning process, like that described previously with reference to the imaging process performed in room 20c.

Also, the camera(s) 120 and the processing unit 102 may perform object(s) monitoring and tracking during treatment planning, like that described previously with reference to the imaging process performed in room 20c.

In addition, the camera(s) 120 and the processing unit 102 may obtain patient data and operation data during treatment planning, like that described previously with reference to the imaging process performed in room 20c.

Furthermore, images obtained by the cameras 120 during treatment planning may be stored in a non-transitory medium (e.g., the database 104), like that described previously with reference to the imaging process performed in room 20c.

FIG. 2C illustrates a user interface 200e with a camera, which may be implemented at a station for treatment planning. The user interface may be implemented using a computer, an iPad, a tablet, an iPhone, a smart phone, or any of other handheld devices. As shown in the figure, the processing unit 102 for treatment planning may perform patient and/or user authentication, patient and/or user verification, components verification, collision avoidance, recording of user and/or patient actions and images, and/or automatic launching of programs.

In some embodiments, the application for treatment planning may include a module for determining possible collision based on images provided by the cameras 120.

III. Simulation Operation

In some embodiments, after the treatment plan is obtained, a simulation operation (like the simulation process 56 of FIG. 1B) may be performed to confirm, improve, and/or modify the treatment plan before an actual treatment is performed on the patient.

In some embodiments, the medical staff performing the treatment simulation may be at a workstation that includes a camera 120. The workstation may be a computer station with a computer, or a handheld device, such as an iPad, a tablet, an iPhone, a smartphone, or any of other handheld devices. Before the medical staff at the treatment simulation station is allowed access to the patient's file and treatment planning software, the camera 120 or another camera may be used to capture an image of the medical staff. The image may then be transmitted to the processing unit 102. The processing unit 102 then accesses the database 104 to retrieve a reference image (e.g., photo) of the medical staff, and compares the image from the camera with the reference image to confirm an identity of the medical staff. After the identity of the medical staff has been confirmed by the processing unit 102, the processing unit 102 then automatically launches the relevant application. Also, after the identity of the patient is confirmed, the processing unit 102 automatically launches the electronic patient file of the patient for the medical staff, and may transmit information in the file to a display for presentation to the medical staff performing the treatment simulation operation. Also, in some embodiments, based on the identity of the user confirmed by the processing unit 102, the processing unit 102 may determine the associated rights of the user of the system for security and safety purposes. For example, if the user is a nurse, then the processing unit 102 may allow the user to perform nursing tasks, and may prevent the user from performing tasks that are reserved for doctors. If a user does not have the permission or associated rights for a task, the processing unit 102 then does not allow the action or task to be initiated or completed by the user.

In some embodiments, the treatment simulation may be performed using a phantom, instead of the actual patient. In other embodiments, the treatment simulation may be performed with the actual patient. In some embodiments, the treatment simulation may be performed on a different day from the treatment. In other embodiments, a treatment simulation may be performed on the same day of treatment, but before treatment energy is delivered to the patient. In further embodiments, a treatment simulation may be performed during a treatment process for the patient.

In some embodiments, simulation may be performed in the room 20h using a simulator 600, which is configured to provide low energy radiation. The simulator 600 has a similar configuration as the treatment system 550 in the treatment room 20d (see FIG. 1A), but is configured to deliver low energy for simulation purpose. In some embodiments, the simulator may have a kV energy source, and a kV diagnostic imager on board. While a treatment simulation is being performed, the cameras 120h in the room 20h and the processing unit 102 of the camera system 10 may be used to perform various functions, like those described previously.

For example, in some embodiments, the camera(s) 120h in the treatment simulation room 20h may be used to perform patient identity confirmation (if a patient is used for the simulation process), like that described previously with reference to the imaging process performed in room 20c. Alternatively, if a phantom is used for the treatment simulation, the camera(s) 120h and the processing unit 102 may perform component identity confirmation (e.g., to confirm an identity of a phantom).

Also, the camera(s) 120h and the processing unit 102 may auto-launch a relevant application and a patient file for the purpose of treatment simulation, like that described previously.

In addition, the camera(s) 120h and the processing unit 102 may perform component(s) verification during the treatment simulation process, like that described previously.

Furthermore, the camera(s) 120h and the processing unit 102 may perform collision avoidance during the treatment simulation process, like that described previously. For example, the processing unit 102 may obtain and analyze images from the camera(s) 120h to determine whether a component of the simulator 600 and a patient may be about to collide, whether a component of the simulator 600 and another component of the simulator 600 may be about to collide, and/or whether a component of the simulator 600 and an external device/accessory/proximate device (e.g., a patient immobilization device, IV poles, resuscitation cart, gurney, an imaging system, a ventilator, an anesthesia cart, a position sensing device (e.g., position sensing cart), a bolus device, a shield, any patient mounted beam modifier, any external device that is not a part of an imaging machine, treatment machine, and/or simulator, but is next to the machine/simulator, etc).

As similarly discussed, collision avoidance may be achieved by the processing unit 102 using three-dimensional models of objects (which represent the geometry of various objects), movement models of the objects (which represent the trajectories and/or degrees of freedom of the objects), and rendering of the real-time camera images from the cameras 120. Based on these information, the processing unit 102 can determine any potential motion hazards. Knowing this information proactively, allows the user to refine the treatment plan before it is approved and before the patient arrives in the department for treatment.

Also, the camera(s) 120h and the processing unit 102 may perform object(s) monitoring and tracking during the treatment simulation process, like that described previously.

In addition, the camera(s) 120h and the processing unit 102 may obtain patient data and operation data during the treatment simulation process, like that described previously.

Furthermore, images obtained by the cameras 120h in the treatment simulation room 20h during the treatment simulation process may be stored in a non-transitory medium (e.g., the database 104).

In some embodiments, when the patient leaves the treatment simulation room 20h after the treatment simulation process, the system 10 automatically captures an image of the patient (e.g., the face of the patient), closes the patient's electronic file, and records all changes.

Figure 2D:
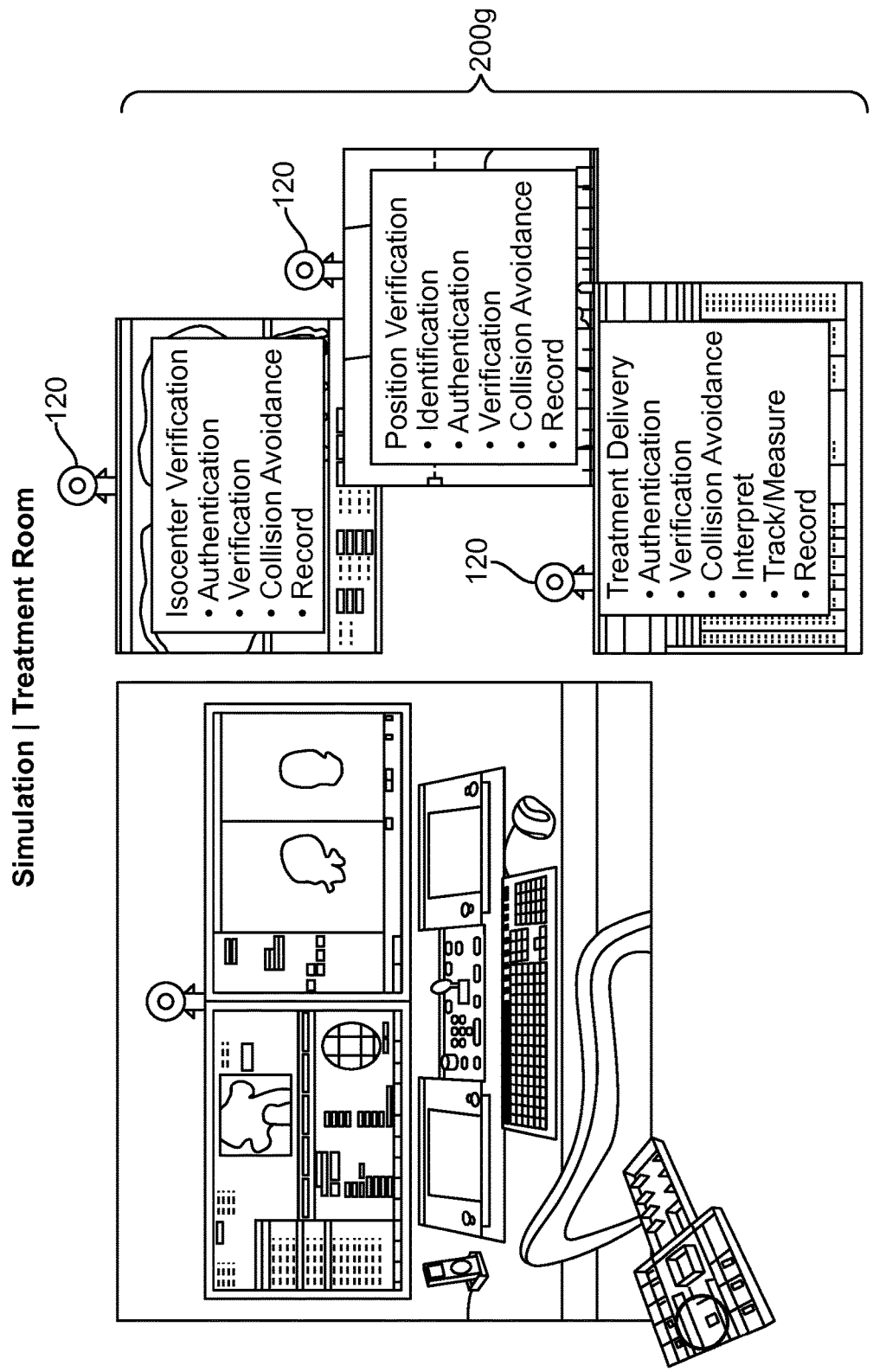
FIG. 2D illustrates cameras implemented at a medical device and at a work station for treatment simulation and/or treatment.

FIG. 2D illustrates a user interface 200g with a camera, which may be implemented at a station for treatment simulation/treatment. The user interface may be implemented using a computer, an iPad, a tablet, an iPhone, a smart phone, or any of other handheld devices. As shown in the figure, the processing unit 102 for treatment simulation (which may involve isocenter verification, position verification, etc.) may perform patient and/or user identification, patient and/or user authentication, patient and/or user verification, components verification, collision avoidance, interpretation of data, track and/or monitor object(s), obtaining of operation data and patient data, recording actions and/or images, and/or automatic launching of programs.

As discussed with reference to FIG. 1B, in some embodiments, after the simulation process 56, a quality assurance process 59 may be performed. If the quality assurance process passes, then treatment may be allowed to be delivered to the patient. If the quality assurance process fails, then additional treatment planning 54 and simulation 56 will be performed until the treatment plan is finalized and approved. As shown in FIG. 2C, in some embodiments, a user interface 200f with a camera may be implemented for plan quality assurance. The user interface may be implemented using a computer, an iPad, a tablet, an iPhone, a smart phone, or any of other handheld devices. As shown in the figure, the processing unit 102 for plan quality assurance may perform patient and/or user authentication, patient and/or user verification, components verification, collision avoidance, recording of user and/or patient actions and images, and/or automatic launching of programs.

As discussed, with reference to FIG. 1B, in some embodiments, information obtained from the simulation process 56 may be used later on for treatment planning 54 (as in a loop-back manner—see arrow 64). In some embodiments, the images captured by the camera(s) 120h and information derived from such images, may be used in a treatment planning process 54 to adjust and/or update an existing treatment plan. For example, in some embodiments, images of object(s) captured by the camera(s) 120*h*, and information derived from such images, such as rendering of object(s), composite images of object(s) (e.g., rendered image of an object superimposed over image of three-dimensional model of the object), may be used to adjust an existing treatment plan.

IV. Treatment Operation

In some embodiments, after the treatment plan and the treatment simulation are performed, a treatment process may then be performed on the patient (like the treatment process 58 shown in FIG. 1B).

In some embodiments, the medical staff performing the treatment may be at a workstation that includes a camera 120, wherein the workstation is configured to operate the treatment radiation system. The workstation may be a computer station with a computer, or a handheld device, such as an iPad, a tablet, an iPhone, a smartphone, or any of other handheld devices. Before the medical staff at the station is allowed access to the patient's file and treatment planning software, the camera 120 or another camera may be used to capture an image of the medical staff. The image may then be transmitted to the processing unit 102. The processing unit 102 then accesses the database 104 to retrieve a reference image (e.g., photo) of the medical staff, and compares the image from the camera with the reference image to confirm an identity of the medical staff. After the identity of the medical staff has been confirmed by the processing unit 102, the processing unit 102 then automatically launches the relevant application. Also, after the identity of the patient is confirmed, the processing unit 102 automatically launches the electronic patient file of the patient (which may include a treatment plan) for the medical staff, and may transmit information in the file to a display for presentation to the medical staff performing the treatment operation. Also, in some embodiments, based on the identity of the user confirmed by the processing unit 102, the processing unit 102 may determine the associated rights of the user of the system for security and safety purposes. For example, if the user is a nurse, then the processing unit 102 may allow the user to perform nursing tasks, and may prevent the user from performing tasks that are reserved for doctors. If a user does not have the permission or associated rights for a task, the processing unit 102 then does not allow the action or task to be initiated or completed by the user.

In some embodiments, treatment may be performed in the treatment room 20*d*, which has the treatment system 550, and the cameras 120*d*.

FIG. 4 illustrates a treatment system 550 in accordance with some embodiments. The radiation system 550 includes an arm gantry 552, a patient support system 554 for supporting a patient 160, and a control system 568 for controlling an operation of the gantry 552 and delivery of radiation. The system 550 also includes a radiation source 572 that projects a beam 576 of radiation towards the patient 160 while the patient 160 is supported on support 554, and a collimator system 555 for changing a cross sectional shape of the radiation beam 576. The radiation source 572 may be configured to generate a cone beam, a fan beam, or other types of radiation beams in different embodiments. Also, in other embodiments, the source 572 may be configured to generate proton beam as a form of radiation for treatment purpose. Also, in other embodiments, the system 550 may have other form and/or configuration. For example, in other embodiments, instead of an arm gantry 552, the system 550 may have a ring gantry 552.

In the illustrated embodiments, the radiation source 572 is a treatment radiation source for providing treatment energy. In other embodiments, in addition to being a treatment radiation source, the radiation source 572 can also be a diagnostic radiation source for providing diagnostic energy for imaging purpose. In such cases, the system 550 will include an imager, such as the imager 580, located at an operative position relative to the source 572 (e.g., under the support 554). In further embodiments, the radiation source 572 may be a treatment radiation source for providing treatment energy, wherein the treatment energy may be used to obtain images. In such cases, in order to obtain imaging using treatment energies, the imager 580 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 572 is able to generate X-ray radiation at a plurality of photon energy levels within a range anywhere between approximately 10 keV and approximately 20 MeV.

In the illustrated embodiments, the control system 568 includes a processing unit 584, such as a processor, coupled to a control 586. The control system 568 may also include a monitor 590 for displaying data and an input device 592, such as a keyboard or a mouse, for inputting data. The operation of the radiation source 572 and the gantry 152 are controlled by the control 586, which provides power and timing signals to the radiation source 572, and controls a rotational speed and position of the gantry 552, based on signals received from the processing unit 584. Although the control 586 is shown as a separate component from the gantry 552 and the processing unit 584, in alternative embodiments, the control 586 can be a part of the gantry 552 or the processing unit 584.

In some embodiments, the system 550 may be a treatment system configured to deliver treatment radiation beam towards the patient 160 at different gantry angles. During a treatment procedure, the source 572 rotates around the patient 160 and delivers treatment radiation beam from different gantry angles towards the patient 160. While the source 572 is at different gantry angles, the collimator 555 is operated to change the shape of the beam to correspond with a shape of the target tissue structure. For example, the collimator 555 may be operated so that the shape of the beam is similar to a cross sectional shape of the target tissue structure. In another example, the collimator 555 may be operated so that different portions of the target tissue structure receive different amount of radiation (as in an IMRT procedure).

As shown in the figure, the radiation system 550 may have multiple cameras 120*d* mounted thereto, or to positions that are next to the radiation system 550. It should be noted that the positions of the cameras 120*d* are exemplary, and that in other embodiments, the camera(s) 120*d* may be mounted at any location on the system 550 and/or in close proximity to it. Although the processing unit 102 is illustrated as a separate component from the radiation system 550, in other embodiments, the processing unit 102, or at least a part of it, may be integrated with the radiation system 550. For example, it may be a part of the control 568 (such as a part of the processing unit 584) in some embodiments.

During the treatment process, the camera system 10 may be used to perform various functions, like those described previously.

IV-A. Patient Identity Confirmation

In some embodiments, when the patient is in the treatment room 20*d*, one or more cameras 120*d* in the room 20*d* then capture one or more images of the patient, and the image(s) is then transmitted to the processing unit 102 for identification of the patient. The processing unit 102 may access the database 104 to determine if there is a match between the image(s) captured by the camera(s) 120*c* with reference image(s) (e.g., photo(s)) stored in the database 104. If a match is found, then the processing unit 102 may identify the patient or confirm the identity of the patient based on the match. For example, if the matched reference image has the patient's name "Mary" associated therewith in the database 104, the processing unit 102 may then determine that the patient in the treatment room 20*d* is "Mary". In some embodiments, the process of patient identification performed by the processing unit 102 may involve feature extraction from the captured image(s), and image comparison between images. In one implementation, image comparison may be achieved by performing cross-correlation between the images. If the cross-correlation is above a prescribed threshold value (e.g., 0.7), then the processing unit 102 may determine that there is a match. In other embodiments, instead of performing image comparison using the processing unit 102, the processing unit 102 may transmit the captured image(s) and reference image(s) of the patient to a display for allowing a user (e.g., a medical staff) to verify the patient identity.

IV-B. Auto-launching of Patient File

After the patient identity has been confirmed (either by the processing unit 102 or by the medical staff), the processing unit 102 may then automatically launch an electronic patient file for the medical staff while the patient is in the treatment room 20*d*. By means of non-limiting examples, the patient file may include the patient's medical chart, operation plan (e.g., treatment plan and/or imaging plan), and any of other information relating to the medical condition and treatment of the patient.

IV-C. Component(s) Verification

In the illustrated embodiments, the operation to be performed on the patient is a treatment procedure. Before the treatment procedure is performed, a setup process may be performed to setup the treatment machine 550 and the patient. For example, a patient immobilization device (e.g., a head frame, a harness, a cuff, etc.) may be used to immobilize at least a portion of the patient. The immobilization device may have one or more features, such as an ID, a marking, etc., for identifying the immobilization device. In some embodiments, one or more cameras 120*d* in the treatment room 20*d* may capture image(s) of the immobilization device, and then transmit the image(s) to the processing unit 102. The processing unit 102 processes the image(s) to verify that the correct immobilization device is being used for the specific patient. For example, the processing unit 102 may perform feature extraction on the image(s) to identify the ID or marking on the immobilization device to determine an identity of the immobilization device. The processing unit 102 also obtains information (e.g., identity information) regarding the correct identity of the immobilization device from an operation plan (which may be included with the patient file accessed by the processing unit 102). The processing unit 102 then compares the identity of the immobilization device derived from processing of the image(s) captured by the camera(s) 120*c* with the identity of the device prescribed in the treatment plan. If there is a match, then the processing unit 102 may determine that the correct immobilization device has been used, and that the setup concerning the immobilization device is correct.

It should be noted that the setup process may involve other medical components, which may or may not be patient-specific, and that the camera(s) 120*c* and the processing unit 102 may be employed to verify the identities of these components in a similar manner. For example, instead of, or in addition to, verifying the patient immobilization device, the camera(s) 120*d* may capture image(s) of other components, such as a collimating cone for attachment to the radiation machine, a filter for attachment to the radiation machine, the patient support system and associated accessories, an imager, a gantry (which may be a ring gantry, an arm gantry, or other types of gantry), IV poles, resuscitation cart, gurney, an imaging system, a ventilator, an anesthesia cart, a position sensing device (e.g., position sensing cart), a bolus device, a shield, any patient mounted beam modifier, etc. The image(s) are transmitted to the processing unit 102 for processing to determine the identity of the component(s). For example, the processing unit 102 may perform feature extraction (e.g., based on text recognition, shape recognition, color recognition, etc.) to determine the identity of the component(s). The processing unit 102 may also obtain the identity of the prescribed component(s) to be used in the operation from a plan that was stored in the database 104, and then compare the identity of the component(s) derived from the image(s) with the prescribed component(s)' identity. If the identity of the component(s) has been verified, then the processing unit 102 may determine that the correct component(s) has been used.

In some embodiments, after the processing unit 102 has verified an identity of the component(s) being used, the processing unit 102 may generate a signal to indicate the result of the verification. For example, the processing unit 102 may generate an audio signal, a visual signal (which may be a light signal, or an image such as a graphic for display in a screen), or both, to inform the medical staff that the correct component(s) is being used. On the other hand, if the processing unit 102 is unable to verify any of the components being used, then the processing unit 102 may generate a signal to prevent the treatment system 550 from being operated to deliver treatment radiation. Alternatively, or additionally, the processing unit 102 may generate a signal, such as an audio signal, a visual signal, or both, to inform the medical staff that the verification cannot be performed. In such medical staff may then conduct further investigation to ensure that the correct component(s) is being used, and may manually confirm the component(s).

In some embodiments, in the alternative to, or in addition to, using the processing unit 102 to verify the component(s), image(s) of the component(s) captured by the camera(s) 120*c* may be displayed together with reference image(s) of the prescribed component(s) retrieved from the database 104 in a screen. The screen may be a computer screen, an iPad screen, a tablet screen, an iPhone screen, a smartphone screen, etc. This allows the medical staff to determine whether the correct component(s) is being used, or to verify the verification result provided by the processing unit 102.

In some embodiments, the processing unit 102 is configured to not allow the radiation system 550 to be operated until all prescribed components have been identified and confirmed.

It should be noted that the camera(s) 120*d* for use to verify component(s) may be the same camera(s) as, or different camera(s) from, the camera(s) for use to verify patient identity. In other embodiments, the camera(s) 120*d* for verifying component(s) may be a subset or a superset of the camera(s) for verifying patient identity.

IV-D. Collision Avoidance

After the component(s) for use in the medical process has been verified, the radiation machine 550 may then be activated to perform the medical process. In the illustrated example, the medical process is a treatment process, and the radiation machine 550 in the treatment room 20*d* is a treatment machine configured to provide radiation treatment energy to treat the patient. However, it should be understood that the system 550 may be other types of treatment system in other embodiments, which may or may not involve radiation as a form of treatment energy. For example, in other embodiments, the system 550 may be configured to deliver other types of energy that are not considered radiation.

In some embodiments, while the radiation source 572 is rotated around the patient 160, one or more cameras 120*d* in the treatment room 20*d* may capture images of the radiation system 550 and the patient 160, and transmit the images to the processing unit 102 for processing. The processing unit 102 processes the images to determine whether there may be a possible collision between two objects that may be happening. The possible collision between two objects may be a possible collision between a component of the radiation system 550 and a person (e.g., the patient 160, a medical staff or personnel, etc.), a component (e.g., gantry 552, source 572, or imager 580) of the radiation system 550 and another component (patient support system 554) of the radiation system 550, or a component of the radiation system 550 and an external device/accessory/proximate device (e.g., a patient immobilization device, IV poles, resuscitation cart, gurney, an imaging system, a ventilator, an anesthesia cart, a position sensing device (e.g., position sensing cart), a bolus device, a shield, any patient mounted beam modifier, any external device that is not a part of an imaging machine, treatment machine, and/or simulator, but is next to the machine/simulator, etc).

Various techniques may be employed in different embodiments for detecting a possible collision using images captured by the cameras 120*d*. In some embodiments, at least two cameras 120*d* are used to capture respective images of the radiation system 550, the patient 160, and other object(s) from different angles. The processing unit 102 may be configured to create three-dimensional rendering of the radiation system 550, the patient 160, and other object(s) using the two-dimensional images from the cameras 120*d*. The three-dimensional rendering may be analyzed by the processing unit 102 to determine if a distance between two objects is within a prescribed threshold. If the distance is within the prescribed threshold, the processing unit 102 may determine that a possible collision may be about to happen, and may generate a signal to indicate such possible collision. The signal may be a warning signal in the form of a visual signal, an audio signal, or both, for informing the medical staff. In addition, or in the alternative, the signal may stop an operation of the radiation system 550. In some embodiments, if the processing unit 102 of the system 10 predicts or detects a possible collision, it may generate a signal to slow down the speed of machine movement in a specified collision warning zone, with resumption of standard motion speed if the zone is cleared. Also, in some embodiments, if a pending collision is detected, the processing unit 102 may generate a signal to stop all motion and beam delivery. In one implementation, there may be a first threshold/criteria for slowing down an operation of the system 550, and a second threshold/criteria for stopping the operation of the system 550. For example, if a distance between two objects is within a first threshold distance, then the processing unit 102 may generate a signal to slow down the operation of the system 550. If the distance between the two objects is within a second threshold distance (which is less than the first threshold distance), then the processing unit 102 may generate a signal to stop the operation of the system 550.

In some embodiments, the three-dimensional composite model of the machine, imager, patient support system (e.g., third party couch top), machine accessories, and immobilization devices, patient specific beam modifying devices, the patient, and proximate equipment may be used by the processing unit 102 to identify and track positions of each entity, and monitor the machine motion trajectory for collision detection and avoidance.

In other embodiments, the processing unit 102 may also obtain three-dimensional model(s) and movement model(s) for tracking different objects in the room. The three-dimensional model represents a geometry (e.g., shape and/or size) of an object (e.g., device component, such as gantry, arm, imager, etc.). The movement model indicates degrees of freedom and/or movement trajectory for one or more objects in the treatment room 20*d*. The three-dimensional model(s) and/or movement model(s) may be generated/determined in a simulation procedure, a planning process, an imaging procedure, and/or a treatment procedure. Alternatively, the three-dimensional model (e.g., the model of the radiation system 550) may be obtained from the manufacturer of the radiation system 550, which has all the geometric data concerning the size and shape of the radiation system 550. The three-dimensional model(s) and movement model(s) may be stored as part of an operation plan (e.g., treatment plan) that is accessed by the processing unit 102. In some cases, there may be different movement models for different components. For example, there may be a first movement model that indicates a movement trajectory or degrees of freedom for the radiation source 572, and a second movement model that indicates a movement trajectory or degrees of freedom for the patient support system 554.

In some embodiments, the movement models may be processed together with the three-dimensional models (e.g., three-dimensional models of the radiation source 572 and the patient support system 554), and the rendering resulted from processing of the camera images, to determine whether a possible collision may be about to happen. For example, based on the physical geometry (e.g., shape and/or size) of the radiation source 572 and the physical geometry (e.g., shape and/or size) of the patient support system 554 (obtained from the three-dimensional models), and based on the direction of movement of the radiation source 572 and/or the patient support system 554 (obtained from the movement models), the processing unit 102 can determine an "expected" image of the scene in the imaging room 20*c*, which shows the expected position of the source 572 and the expected position of the support system 554. The processing unit 102 may then compare the rendering (which represents the real-time configuration of the source 572 and the support system 554) resulted from processing of the real-time camera images with the expected image. If rendering does not match the expected image, this indicates that the behavior of the system 150 does not match the expected behavior (e.g., the position of the gantry/source does not match the expected position). In such cases, the processing unit 102 may generate a signal to stop the operation of the treatment system 550 to prevent any possible object collision. In some embodiments, the rendering (derived from the camera image(s)) may be superimposed over the expected image (derived from the three-dimensional model(s) and the movement model(s) to generate a composite image. The composite image may be presented in a screen for presentation to a user, so that the user can visualize in real-time what the actual configuration of the objects (e.g., components and/or patient) is, versus the expected configuration of the objects (e.g., components and/or patient).

In other embodiments, the one or more cameras 120*d* may be one or more depth sensing cameras, which may be used to sense distances measured from a reference location to points on a surface of an object, or to points on different surfaces of different objects. In such cases, the output from the depth sensing camera(s) 120*d* may be used to determine the shapes of different objects, and/or distances between different points on different objects from a reference location. The shapes of different objects and/or the distances may then be used to determine positions of objects and/or whether two objects are close enough to indicate that a possible collision may be about to happen.

In some embodiments, the depth sensing camera 120*d* may use structured light for depth measurement (e.g., a Kinect camera). In other embodiments, the depth sensing camera 120*d* may use time-of-flight method for depth measurement (e.g., Mesa SR4000, or the new Microsoft Kinect2 camera). In further embodiments, the depth sensing camera 120*d* may be any device that is capable of sensing depth using any known techniques. It should be noted that the term "camera", as used in this specification, may be any device, and should not be limited to a device that provides "image" signals. For example, in some embodiments, the depth sensing camera 120*d* may be configured to provide depth signals, which may or may not be considered image signals, regardless of whether such depth signals are displayed in image form or not. A depth signal may be any signal indicating a depth or distance, or any signal from with a depth or distance may be derived. By means of non-limiting examples, the signal may be an infrared signal, an ultrasound signal, etc.

Also, in some embodiments, the depth sensing camera 120*d* may be infrared-based, in which cases, the depth may be sensed by the camera 120*d* using infrared. In some embodiments, such depth sensing camera 120*d* may be configured to output infrared video images from which depth images are formed. In some embodiments, these infrared video images may have exactly the same field of view as the depth images. Thus, the infrared video images may be used together with the depth images to determine whether there is a possible collision.

Furthermore, in some embodiments, the depth sensing camera 120*d* may include an infrared emitter, a color sensor, and an infrared depth sensor. The infrared depth sensor is configured to sense depth based on infrared signals output by the infrared emitter. The color sensor is configured to sense visible image. The depth signals and the visible image may then be used together by the processing unit 102 to determine whether there may be a possible collision that may be about to happen.

Also, in further embodiments, a depth sensing camera 120*d* may be used to capture a reference depth image of the radiation system 550 and the patient 160. During the imaging process, the depth sensing camera 120*d* generates multiple depth images in real time, and each of the real time depth images is subtracted from the reference depth image, or vice versa, to obtain a difference image. Values in the difference image within a region of interest are then analyzed by the processing unit 102 to determine if any of the values exceeds a threshold level. If so, then the processing unit 102 may determine that there is a possible collision that may be happening. Techniques using image subtraction to determine a possible collision has been disclosed in U.S. patent application Ser. No. 13/926,912, filed on Jun. 25, 2013, the entire disclosure of which is expressly incorporated by reference herein.

In the illustrated embodiments, the processing unit 102 is configured to automatically detect a possible collision. In other embodiments, a user may also participate in determining whether there is a possible collision. For example, in some cases, a screen (e.g., a computer screen, an iPad screen, a tablet screen, an iPhone screen, a smart phone screen, or any of other handheld device screens) may be used to continuously display the real time images from camera(s) and/or images (e.g., images of a three-dimensional model(s), images of rendering, composite images, etc.) derived by the processing unit 102 during the procedure, so that the person operating the treatment procedure may view the images and identify possible collisions. In one or more embodiments, the depth image and the optical image may be superimposed/overlaid to obtain a composite image that shows both depth and visible image.

In some embodiments, the processing unit 102 of the system 10 may provide a user interface for display in a screen (e.g., a computer screen, an iPad screen, a tablet screen, an iPhone screen, a smart phone screen, or a screen of any handheld devices), wherein in the user interface, directional arrow(s) (or other indicator(s)) indicating machine motion(s) is presented over a real time display of the three-dimensional composite model or over the real-time image. These overlays will allow the user to visualize the direction a moving part is planned to be moving. When a collision or collision warning zone is detected, the entities will be identified to the user by highlight on the real time display of the three-dimensional composite model or the real-time image.

In some embodiments, the images captured during the operation of the radiation system 550 may be stored in a non-transitory medium, such as the database 104. This allows the images to be reviewed later if necessary.

It should be noted that the camera(s) 120*d* for use to detect possible collision may be the same camera(s) as, or different camera(s) from, the camera(s) for verifying component(s) and/or for verifying patient identity. In other embodiments, the camera(s) 120*d* for detecting possible collision may be a subset or a superset of the camera(s) for verifying component(s) and/or for verifying patient identity.

IV-E. Object(s) Monitoring and Tracking

In some embodiments, during operation of the radiation system 550, one or more cameras 120*d* in the treatment room 20*d* may capture images for monitoring and/or tracking object(s). For example, the captured images may include images of the patient. In such cases, the processing unit 102 receives the images, and processes the images to monitor the patient.

In some embodiments, the processing unit 102 may process the images to determine whether the patient has moved away from a desired position. For example, the patient may have shifted away from the desired position, but may still remain in a field of view of the camera(s). In another example, the patient may have moved completely away so that the patient is no longer in the field of view of the camera(s), in which cases, the processing unit 102 may be configured to detect absence of the patient. If the patient has moved away from a desired position, then the processing unit 102 may generate a signal to stop the operation of the radiation system 150, and/or a signal to inform the medical staff. Otherwise, the processing unit 102 may let the operation of the radiation system 150 continue.

Also, some embodiments, the processing unit 102 may process the images to confirm that the patient is in the operative position or next to (e.g., in front of) the treatment machine while radiation is being delivered (e.g., during beam-on operation). If the patient cannot be detected by the camera(s) and the processing unit 102, then the processing unit 102 may generate a signal to stop the operation of the treatment system 550, and/or a signal to inform the medical staff. Otherwise, the processing unit 102 may let the operation of the treatment system 550 continue.

In other embodiments, the processing unit 102 may process the images to determine whether there is patient movement or not. If the patient has moved, then the processing unit 102 may generate a signal to stop the operation of the radiation system 150, and/or a signal to inform the medical staff. Otherwise, the processing unit 102 may let the operation of the radiation system 550 continue.

In further embodiments, the processing unit 102 may process the images to determine physiological movement (e.g., breathing motion). For example, the processing unit 102 may process the images to determine breathing amplitudes and/or breathing phases of the patient during operation of the radiation system 550. The determined physiological movement may be used to gate an operation of the radiation system 550. For example, in some embodiments, the processing unit 102 may be configured to generate a signal for activating the radiation source when the breathing amplitude is within a prescribed amplitude range, or when a breathing phase is within a prescribed phase range. In other embodiments, the processing unit 102 may be configured to generate a signal for de-activating the radiation source when the breathing amplitude is within a prescribed amplitude range, or when a breathing phase is within a prescribed phase range. Also, in further embodiments, the processing unit 102 may be configured to generate a signal to move the radiation source 572 and/or the patient support system 554 based on the determined physiological movement.

In other embodiments, the images captured by the camera(s) 120d may include images of one or more medical device components. In such cases, the processing unit 102 receives the images, and processes the images to monitor the medical device component(s). For example, the processing unit 102 may determine the position of a medical device component (e.g., the radiation source 572, the patient support system 554, or the imager 580) based on an analysis of the images. In some cases, the determined position may be used to confirm an intended position of the medical device component, as similarly discussed. For example, in some embodiments, three-dimensional model of a component and a movement model of the component may allow the processing unit 102 to determine an "expected" image that shows the expected position of the component at a certain time. The real-time camera image(s) may be processed by the processing unit 102 to determine a rendering of the component that shows the three-dimensional configuration of the component in real time. The three-dimensional rendering may then be compared with the expected image to determine whether the component is at the intended position or not.

In some embodiments, the images captured during the operation of the radiation system 550 may be stored in a non-transitory medium, such as the database 104. This allows the images to be reviewed later if necessary.

It should be noted that the camera(s) 120d for monitoring and/or tracking object(s) may be the same camera(s) as, or different camera(s) from, the camera(s) for verifying component(s), for verifying patient identity, and/or for detecting possible collision. In other embodiments, the camera(s) 120d for monitoring and/or tracking object(s) may be a subset or a superset of the camera(s) for verifying component(s), for verifying patient identity, and/or for detecting possible collision.

IV-F. Obtaining of Patient Data and Operation Data

In some embodiments, before, during, and/or after operation of the radiation system 550, one or more cameras 120d in the treatment room 20d may capture one or more images for obtaining operation data. For example, in some embodiments, the image(s) may be transmitted to the processing unit 102, which processes the image(s) to determine a patient shape. In other embodiments, the processing unit 102 may process the image(s) to determine patient habitus and size. In further embodiments, the processing unit 102 may process the image(s) to determine a source-to-skin distance. In other embodiments, the processing unit 102 may process the image(s) to determine object distance from isocenter, wherein the object may be a component (such as a radiation source, an imager, etc.), or a part of a patient. In still further embodiments, the processing unit 102 may process the image(s) to determine distance between two objects. The two objects may be a component of a radiation system and a patient, two components of a radiation system, or a component of a radiation system and an external device/accessory.

In some embodiments, the patient data and/or operation data obtained using the camera system 10 may be processed by the processing unit 102 to determine whether a condition (e.g., patient size has changed, patient position has changed, etc.) has met to automatically trigger an imaging process, a simulation process, and/or a treatment planning process, during the treatment of the patient.

Various techniques may be employed to determine operation data and/or patient data using image(s) obtained from the camera(s) 120d. In some embodiments, two-dimensional images obtained by multiple cameras 120d from different angles may be processed to determine three-dimensional shapes of different objects. Then distance between the objects may be calculated. In other embodiments, a distance between two locations in a reference image may be pre-determined (e.g., through a calibration process), and then an image from a camera 120d may be analyzed (using geometric principles and scaling) to determine a distance between two locations in the image. In still further embodiments, the one or more cameras 120d may be one or more depth sensing cameras, which may be used to sense distances measured from a reference location to points on a surface of an object, or to points on different surfaces of different objects. In such cases, the output from the depth sensing camera(s) 120d may be used to determine the shapes of different objects, and/or distances between different points on different objects from a reference location.

Thus, in some embodiments, a system for use in a medical process includes: one or more cameras for providing one or more images; and a processing unit configured to receive the one or more images; wherein the processing unit is configured to process one or more images to determine a body shape and/or size of a patient.

In other embodiments, a system for use in a medical process includes: one or more cameras for providing one or more images; and a processing unit configured to receive the one or more images; wherein the processing unit is configured to process the one or more images to determine a source-to-skin distance.

In further embodiments, a system for use in a medical process includes: one or more cameras for providing one or more images; and a processing unit configured to receive the one or more images; wherein the processing unit is configured to process one or more images to determine an object distance from isocenter.

In still further embodiments, a system for use in a medical process includes: one or more cameras for providing one or more images; and a processing unit configured to receive the one or more images; wherein the processing unit is configured to process one or more images to determine a spatial distance between two objects.

IV-G. Record Data

In some embodiments, images obtained by the cameras 120*d* in the treatment room 20*d* may be stored in a non-transitory medium, such as the database 104. Also, actions taken, tasks completed, operations of the radiation system 550, and user interactions (with the radiation system 550, applications, and patient file) may be stored in the non-transitory medium.

In some embodiments, the camera system 10 may include a user interface for providing a playback feature so that a user of the camera system 10 may view the images on a screen. For example, the user interface may be provided on a screen of a computer, an iPad, a tablet, an iPhone, a smartphone, or any of other handheld devices, so that the user can view the images. The images may be transmitted from the database 104 to the device with the user interface through a network connection. In some embodiments, the user interface may display the images in a playback configuration so that the user can view the images in a video format. Also, the user interface may display information regarding actions taken, tasks completed, operations of the radiation system 550, and user interactions (with the radiation system 550, applications, and patient file), simultaneously with the images in the screen.

The playback feature may be used as documentation, observation, and/or review of the operation, and/or for treatment planning (e.g., for additional treatment). The playback feature may allow clinicians to visualize all actions taken during the operation using the radiation system 550 for quality assurance purposes. Additionally, the data for the playback feature may be used for clinical trials, outcome predictions, and legal review.

In some embodiments, when the patient leaves the treatment room 20*d* after treatment, the system 10 automatically captures an image of the patient (e.g., the face of the patient), closes the patient's electronic file (e.g., treatment plan), and records all changes.

As discussed, with reference to FIG. 1B, in some embodiments, information obtained from the treatment process 58 may be used later on for treatment planning 54 (as in a loop-back manner—see arrow 64). In some embodiments, the images captured by the camera(s) 120*d* and information derived from such images, may be used in a treatment planning process 54 to plan for the next treatment. For example, in some embodiments, images of object(s) captured by the camera(s) 120*d*, and information derived from such images, such as rendering of object(s), composite images of object(s) (e.g., rendered image of an object superimposed over image of three-dimensional model of the object), may be used to determine a treatment plan for the next treatment. Such information contains information on how the treatment system 550 perform and how well the previous treatment plan was executed, and therefore may be used to determine a future treatment plan (e.g., update an existing treatment plan for a future treatment).

FIG. 2D illustrates a user interface 200*g* with a camera, which may be implemented at a station for treatment. The user interface may be implemented using a computer, an iPad, a tablet, an iPhone, a smart phone, or any of other handheld devices. As shown in the figure, the processing unit 102 for treatment (which may involve isocenter verification, position verification, etc.) may perform patient and/or user identification, patient and/or user authentication, patient and/or user verification, user permissions, components verification, collision avoidance, interpretation of data, track and/or monitor object(s), obtaining of operation data and patient data, recording actions and/or images, and/or automatic launching of programs.

Also, as shown in FIG. 2E, in some embodiments, a user interface 200*h* with a camera may be implemented for offline treatment quality assurance. The user interface may be implemented using a computer, an iPad, a tablet, an iPhone, a smart phone, or any of other handheld devices. As shown in the figure, the processing unit 102 for treatment quality assurance may perform user authentication, user verification, recording of user actions and images, and/or automatic launching of programs.

Also, as shown in FIG. 2E, in some embodiments, a user interface 200*i* with a camera may be implemented for billing. The user interface may be implemented using a computer, an iPad, a tablet, an iPhone, a smart phone, or any of other handheld devices. As shown in the figure, the processing unit 102 for billing may perform user authentication, user verification, recording of user actions and images, and/or automatic launching of programs.

In one or more embodiments described herein, the camera system 10 may be used to identify that a patient is in a specific room in a department, and/or automatically opening the relevant file(s) and software program(s) according to the type of room they are in. For example, if the patient is in the exam room 20*d* or the MD office 20*e*, then the processing unit 102 may automatically launch the patient's medical chart. If the patient is in the treatment room 20*d*, then the processing unit 102 may automatically launch a treatment plan that has been specifically determined for the patient, and the treatment software.

Although the above embodiments have been described with reference to radiation treatment, in other embodiments, the imaging system 10 may be implemented for any medical process, which may or may not involve radiation. For example, in other embodiments, the treatment process may not be a radiation treatment process, and may be any procedure for treating a patient.

Processing of Images from Camera(s)

As discussed, in some embodiments, the camera system 10 may be used to track and/or monitor one or more objects during an imaging process, treatment process, simulation process, and/or treatment process. An object may be any machine component, a person (e.g., patient, nurse, doctor, operator, medical staff, etc.), a device, etc. In some embodiments, the tracking and/or monitoring of object(s) may be performed by the processing unit 102 using camera images captured by the camera(s) 120, three-dimensional geometric model of object(s), and movement model of object(s).

Figure 9A:
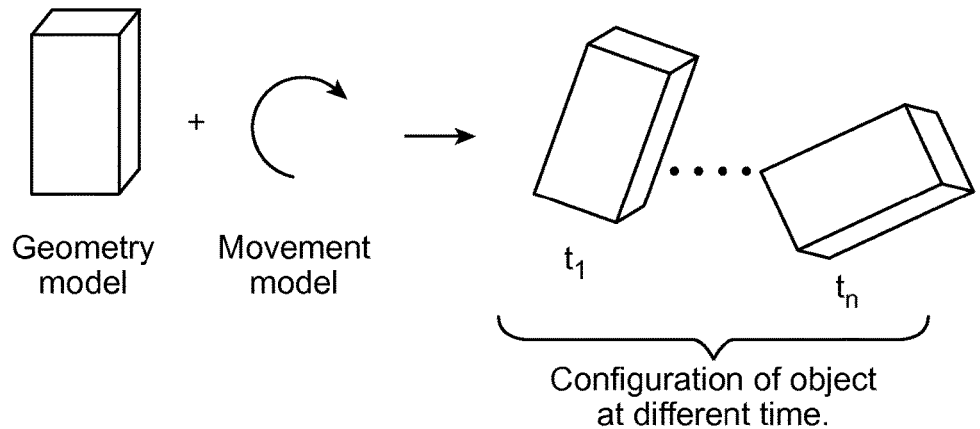
FIG. 9A illustrates a processing of a three-dimensional geometric model and a movement model.

In particular, in some embodiments, the processing unit 102 may obtain a three-dimensional geometric model that represents a geometry of an object. Alternatively, the three-dimensional geometric model may represent multiple geometries of multiple respective objects. For example, the three-dimensional geometric model may have a first sub-3D model that represents the geometry of a first object, and a second sub-3D model that represents the geometry of a second object that is different from the first object. A three-dimensional geometric model represents the geometry of an object, such as the shape, size, extent, etc. of the object. FIG. 9A illustrates an example of a three-dimensional geometric model of an object having a rectangular-block configuration. The model defines the shape, size, and extent of the object.

The processing unit 102 also obtains a movement model that represents a trajectory and/or degrees of movement of an object. Alternatively, the movement model may represent trajectories and/or degrees of movement of multiple respective objects. For example, the movement model may have a first sub-movement model that represents the trajectory and/or degree of movement of a first object, and a second sub-movement model that represents the trajectory and/or degree of movement of a second object that is different from the first object. FIG. 9A illustrates an example of a movement model for an object having a rectangular-block configuration. The model defines the trajectory of the object. In some cases, the movement model also defines the speed of the movement and/or a timing of the movement (which may be derived from a plan, such as a treatment plan).

As shown in FIG. 9A, the three-dimensional model and the movement model may be processed together by the processing unit 102 to determine the different configurations of the object at different time. Each of the configurations represents the expected configuration of the object at a certain time. By knowing this, and by comparing this with the real-time images of the object during a medical process, the processing unit 102 can track and/or monitor the object to determine whether object is at the right position at the right time, or not.

Figure 9B:
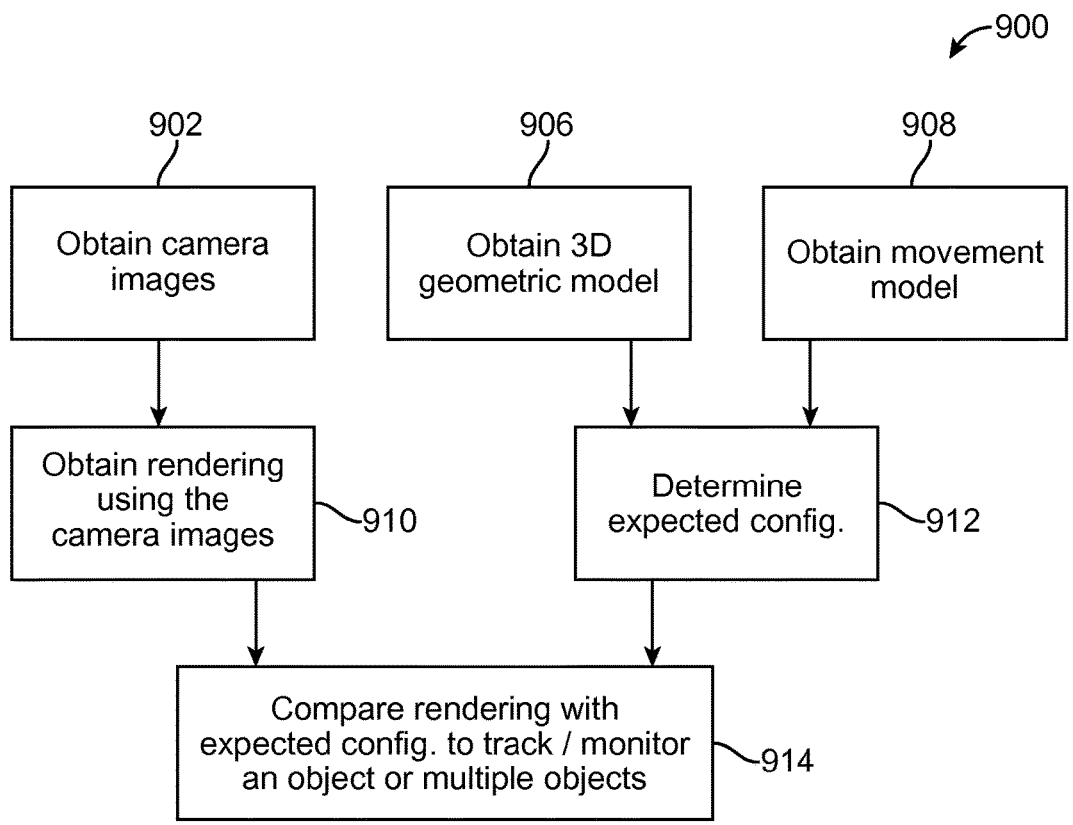
FIG. 9B illustrates a method of monitoring and/or tracking an object.

FIG. 9B illustrates the above process. As shown in the method 900 of FIG. 9B, in some embodiments, the processing unit 102 obtains real-time camera images from the camera(s) 120 of the camera system 10 (item 902). The processing unit 102 also obtains three-dimensional model of object(s) (item 906), and obtains movement model of the object(s) (item 908).

The processing unit 102 then determines a rendering using the real-time camera images, which represents an actual three-dimensional configuration of the object(s) at a certain time (item 910). In some embodiments, the rendering may be determined using images from cameras 120 at different positions aimed at the object(s) from different angles.

The processing unit 102 also determines a configuration of the object(s) representing the expected configuration of the object(s) at the time (item 912). The expected configuration identifies the shape, size, position, and extent of the object(s) at the given time.

As shown in the figure, in item 914, the processing unit 102 may compare the rendering with the expected configuration of the object(s) to track and/or monitor the object(s). For example, in some embodiments, the rendering may be superimposed with the expected configuration of the object(s) to see if they match up. If so, that means the object(s) is at the correct and expected position. Also, the superimposed images may be presented on a screen for display to a user in some embodiments.

In some embodiments, items 902, 910, 912, and 914 may be repeated for additional images from the cameras 120 generated at different times to continuously monitor the object(s) during a medical process.

In some embodiments, the method 900 may be used to track and/or monitor multiple objects simultaneously. In such cases, the expected configuration of the different objects may be determined based on the 3D models (e.g., sub-models) of the respective objects and movement models (e.g., sub-movement models) of the respective objects. The expected configuration of the multiple objects is then compared with the rendering from item 910, which represents the actual configuration of the multiple objects at a given time.

In some embodiments, to speed up computation and processing time, and/or to reduce an amount of required processing resource, the processing unit 102 may take into consideration of whether object(s) or portion(s) of an object is stationary (static) or moving (dynamic). For example, when processing camera images, static object (such as background) may be subtracted out before they are rendered and/or compared with the expected configuration of the object(s).

Also, in some embodiments, the expected configuration of the object(s) may be presented as a "scene" that represents what an expected image should look like.

In addition, in some embodiments, the rendering in item 910 may not be required. For example, in some embodiments, the expected configuration of the object(s) in item 912, which contains three-dimensional information of the object(s), may be projected to a two-dimensional camera view of one of the cameras 120. In such cases, the real-time image of the camera 120 may be directly compared with the projected image to track and/or monitor the object(s).

Examples of Cameras Implemented in a Medical Facility Room

As discussed, an imaging/treatment room in a medical facility may include one or more cameras 120.

Figure 5A:
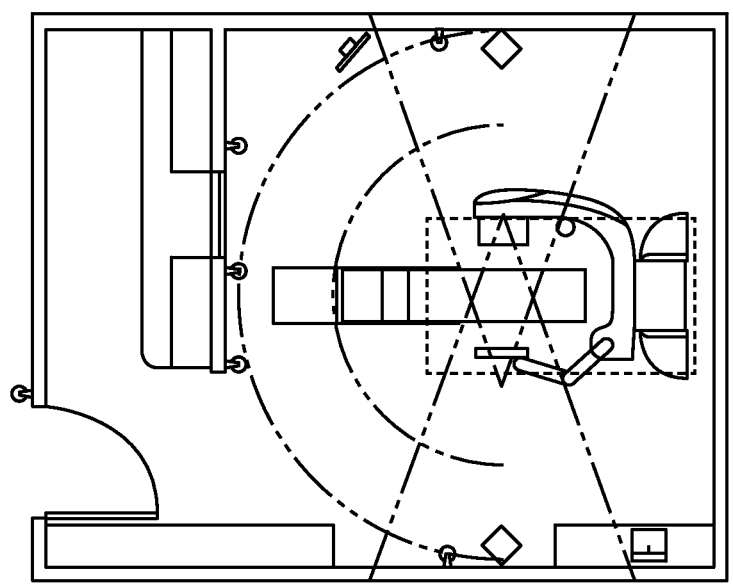
FIGS. 5A-5B illustrate cameras implemented in a standard simulation room in accordance with some embodiments.
Figure 5B:
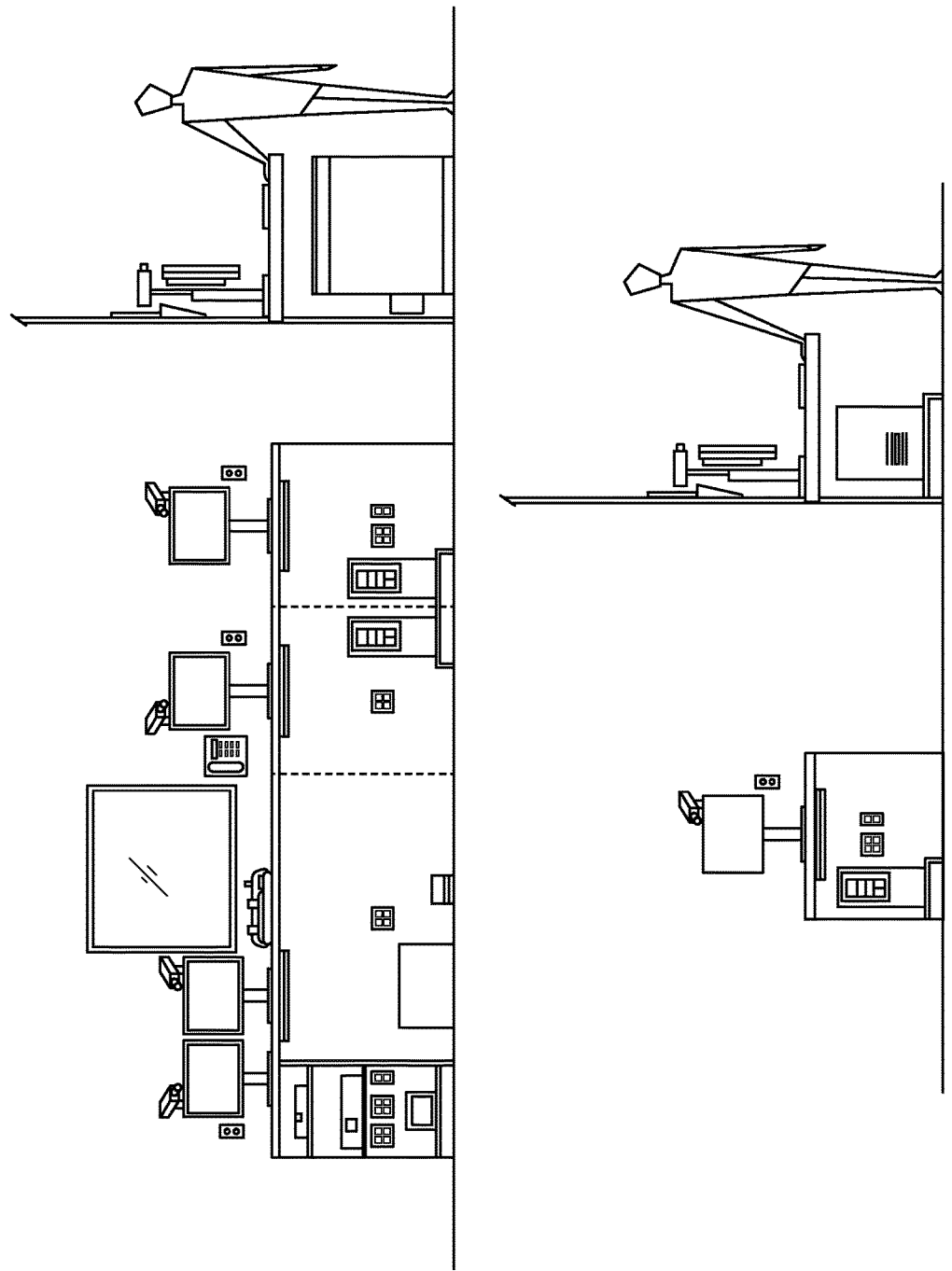

FIGS. 5A-5B illustrate an example of cameras implemented in a medical facility in accordance with some embodiments. As shown in FIG. 5A, which is a plan view of a treatment room with a radiation system, there may be multiple cameras 120 mounted to walls and/or ceiling (indicated by item "1"), a ceiling mounted camera (indicated by item "2"), and a gantry-mounted camera (indicated by item "3"). These cameras, either individually, or in combination, together with the processing unit 102 may be configured to perform any of the functions described herein, including but not limited to patient identification confirmation, object (e.g., patient and device component(s)) verification, preventing collision between two objects, patient monitoring, object tracking, obtaining of operation data, and any combination of the foregoing. Also, as shown in FIG. 5B, the station for controlling the radiation system may have multiple cameras at respective computers/screens. The cameras together with the processing unit 102 may be used to perform any of the functions described herein, including but not limited to user identification confirmation, automatic launching of relevant programs, etc.

Figure 6A:
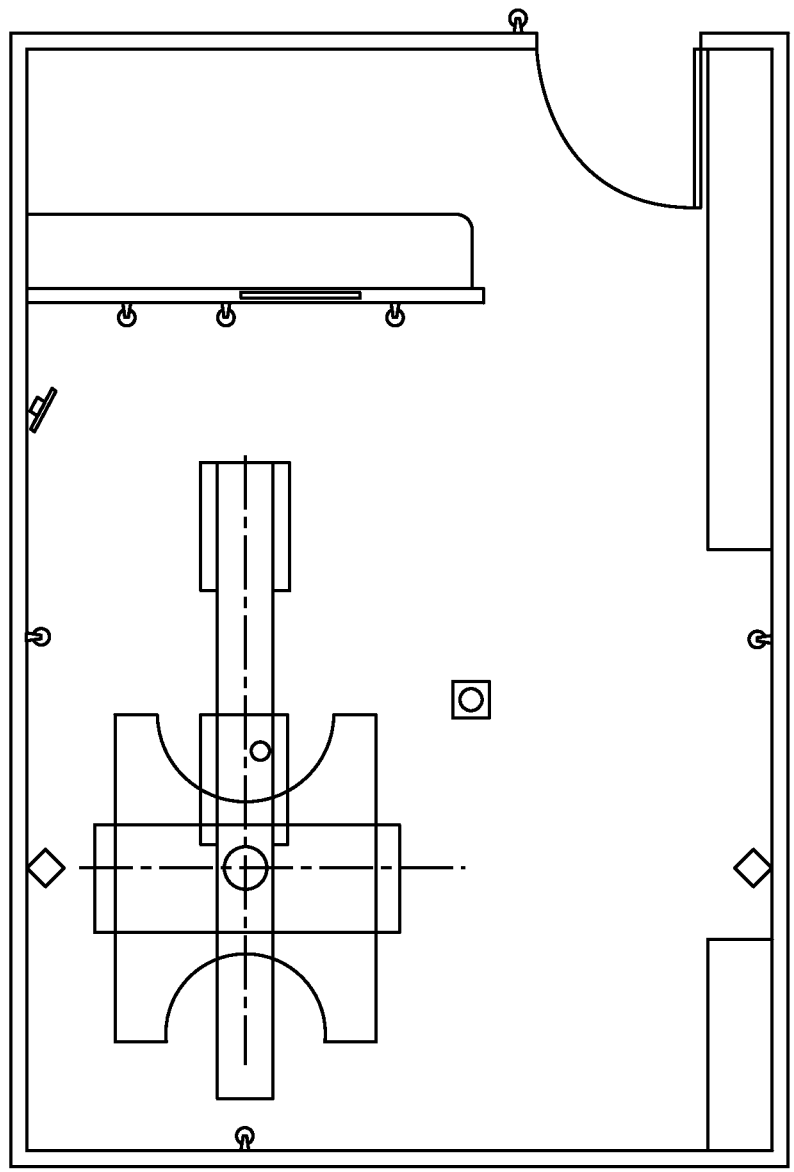
FIGS. 6A-6B illustrate cameras implemented in a CT Simulation room in accordance with some embodiments.
Figure 6B:
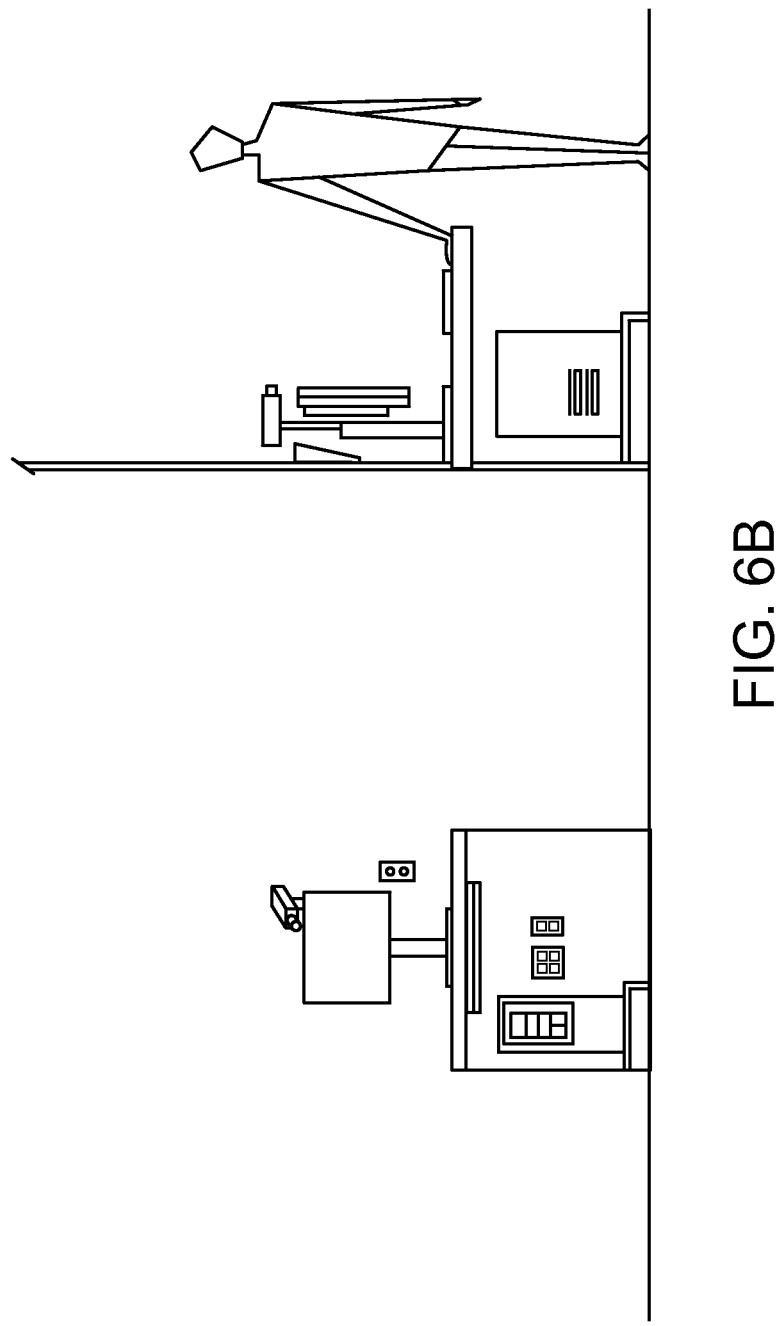

FIGS. 6A-6B illustrate another example of cameras implemented in a medical facility in accordance with some embodiments. As shown in FIG. 6A, which is a plan view of an imaging/simulation room with a radiation system, there may be multiple cameras 120 mounted to walls and/or ceiling (indicated by item "1"), and a ceiling mounted camera (indicated by item "2"). These cameras, either individually, or in combination, together with the processing unit 102 may be configured to perform any of the functions described herein, including but not limited to patient identification confirmation, object (e.g., patient and device component(s)) verification, preventing collision between two objects, patient monitoring, object tracking, obtaining of operation data, and any combination of the foregoing. Also, as shown in FIG. 6B, the station for controlling the radiation system may have a camera. The camera together with the processing unit 102 may be used to perform any of the functions described herein, including but not limited to user identification confirmation, automatic launching of relevant programs, etc.

Figure 7A:
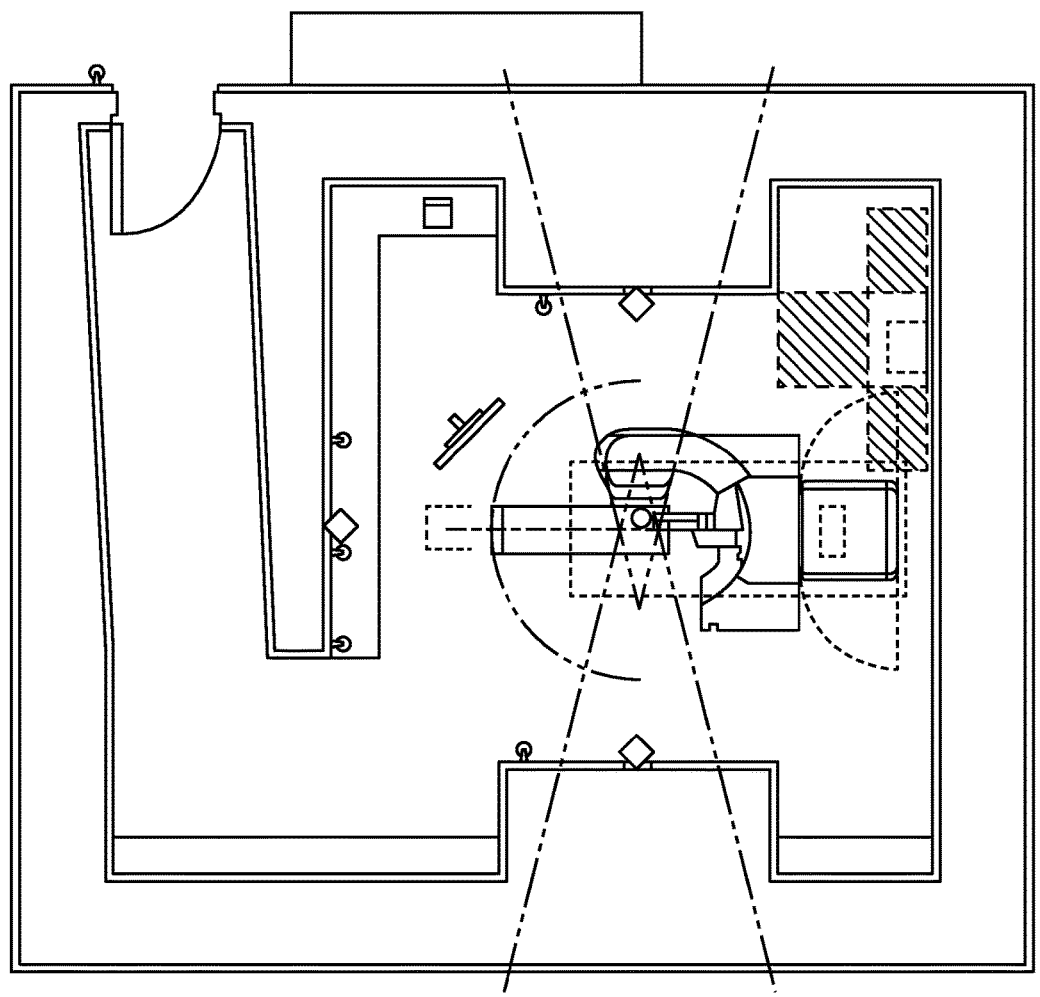
FIGS. 7A-7B illustrate cameras implemented in a treatment room in accordance with some embodiments.
Figure 7B:
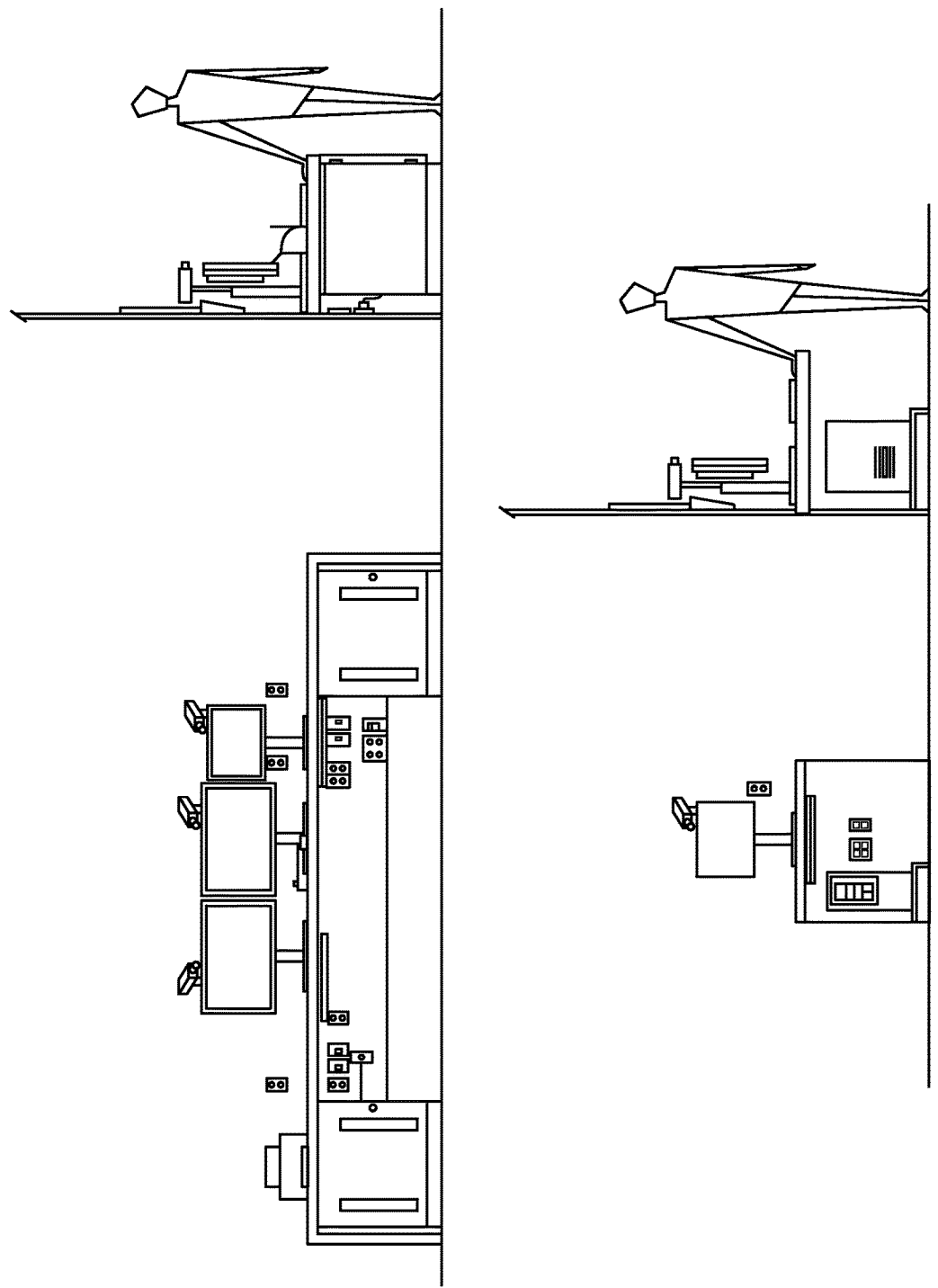

FIGS. 7A-7B illustrate another example of cameras implemented in a medical facility in accordance with some embodiments. As shown in FIG. 7A, which is a plan view of a treatment room with a high energy radiation system, there may be multiple cameras 120 mounted to walls and/or ceiling (indicated by item "1"), a ceiling mounted camera (indicated by item "2"), a gantry-mounted camera (indicated by item "3"), and a camera at a live view location (indicated by item "4"). These cameras, either individually, or in combination, together with the processing unit 102 may be configured to perform any of the functions described herein, including but not limited to patient identification confirmation, object (e.g., patient and device component(s)) verification, preventing collision between two objects, patient monitoring, object tracking, obtaining of operation data, and any combination of the foregoing. Also, as shown in FIG. 7B, the station for controlling the radiation system may have cameras at respective computers/screens. The cameras together with the processing unit 102 may be used to perform any of the functions described herein, including but not limited to user identification confirmation, automatic launching of relevant programs, etc.

Figure 8A:
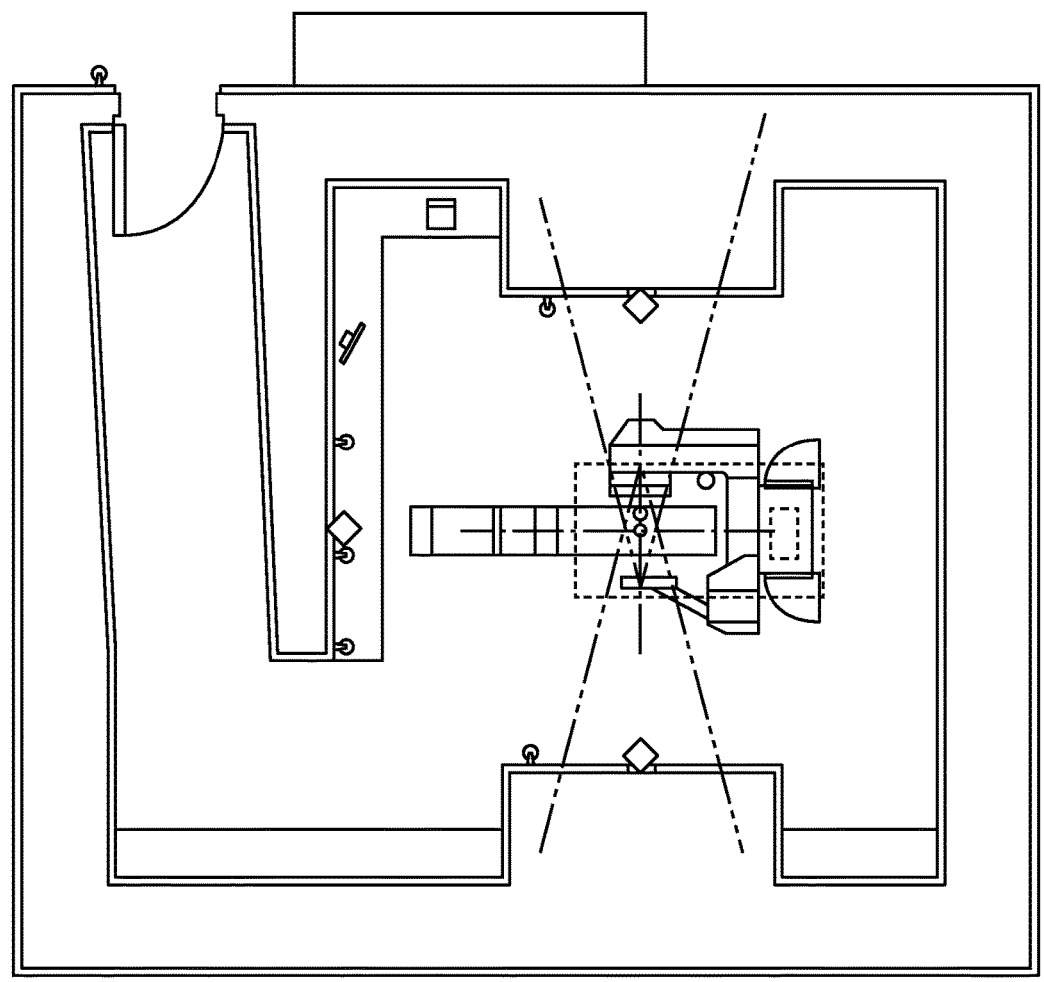

FIGS. 8A-8B illustrate another example of cameras implemented in a medical facility in accordance with some embodiments. As shown in FIG. 8A, which is a plan view of a treatment room with a low energy radiation system, there may be multiple cameras 120 mounted to walls and/or ceiling (indicated by item "1"), a ceiling mounted camera (indicated by item "2"), a gantry-mounted camera (indicated by item "3"), and a camera at a live view location (indicated by item "4"). These cameras, either individually, or in combination, together with the processing unit 102 may be configured to perform any of the functions described herein, including but not limited to patient identification confirmation, object (e.g., patient and device component(s)) verification, preventing collision between two objects, patient monitoring, object tracking, obtaining of operation data, and any combination of the foregoing. Also, as shown in FIG. 8B, the station for controlling the radiation system may have cameras at respective computers/screens. The cameras together with the processing unit 102 may be used to perform any of the functions described herein, including but not limited to user identification confirmation, automatic launching of relevant programs, etc.

Computer System Architecture

Figure 10:
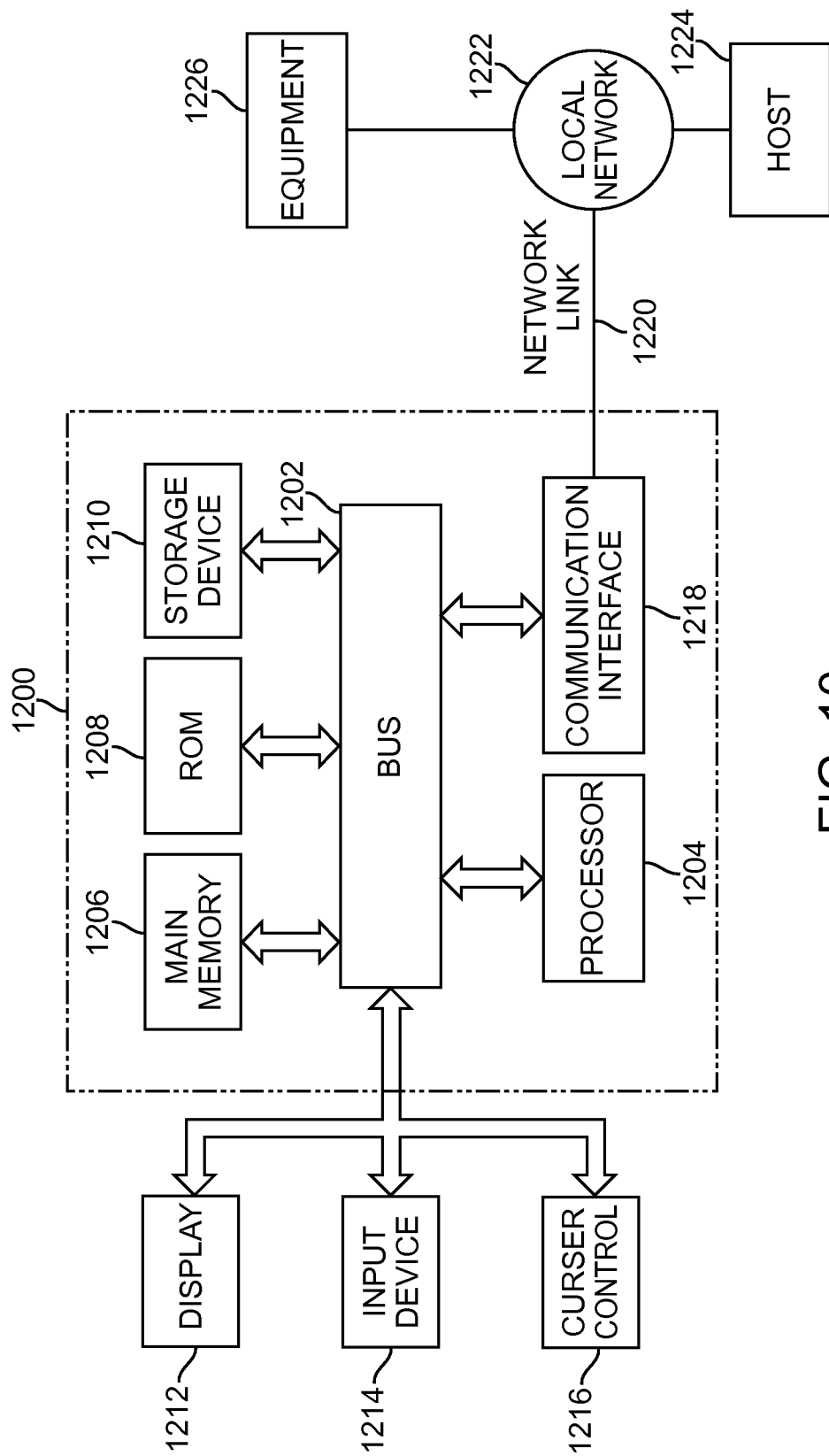
FIG. 10 illustrates a computer system with which embodiments described herein may be implemented.

FIG. 10 is a block diagram illustrating an embodiment of a computer system 1600 that can be used to implement various embodiments described herein. For example, the computer system 1600 may be configured to implement a workstation/user interface for any of the areas/rooms in a treatment facility in accordance with some embodiments. Also, in some embodiments, the computer system 1600 may be used to implement the processing unit 102 described herein. Computer system 1600 includes a bus 1602 or other communication mechanism for communicating information, and a processor 1604 coupled with the bus 1602 for processing information. In some embodiments, the processor 1604 may be an example of the processing unit 102, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method of monitoring an object during a medical process, comprising:

using one or more cameras to obtain information regarding a three dimensional object involved in a medical process, the object being a part of a medical system, the medical system having an energy source configured to deliver energy towards a patient from a distance;

obtaining a three-dimensional model of the object representing a geometry of the object, wherein the three-dimensional model of the object is created without using the one or more cameras;

obtaining a movement model of the object, wherein the movement model of the object indicates degrees of freedom of a machine component and/or a predetermined trajectory of the machine component; and processing the information, the three-dimensional model, and the movement model to monitor the object during the medical process, wherein the act of processing is performed using a processing unit;

wherein at least one of the cameras comprises multiple sensors configured to sense multiple respective distances from respective points on a surface, wherein the sensors are identical to each other; and wherein the act of processing comprises determining an expected three-dimensional extent of the object for an expected position and an expected orientation of the object, and wherein the expected three-dimensional extent of the object is determined using the three-dimensional model and the movement model of the object.

2. The method of claim 1, wherein the one or more cameras comprise a depth sensing camera.

3. The method of claim 1, wherein the one or more cameras comprise a plurality of cameras, and the information comprises a three-dimensional rendering of the object obtained using images from the cameras.

4. The method of claim 1, wherein the act of processing further comprises comparing the expected three-dimensional configuration of the object with a three-dimensional rendering of the object obtained using images from the one or more cameras.

5. The method of claim 1, wherein the medical system comprises a treatment machine, an imaging device, or a radiation machine.

6. The method of claim 1, wherein the object is monitored to determine if there is a possible collision between the object and the patient, or between the object and another object.

7. The method of claim 1, wherein the one or more cameras comprises a camera coupled to a linear accelerator, a radiation treatment machine, a radiation imaging device, or a patient support system.

8. The method of claim 1, wherein the one or more cameras comprises a plurality of cameras coupled to a linear accelerator, a radiation treatment machine, a radiation imaging device, a patient support system, or a combination of the foregoing.

9. The method of claim 1, wherein the one or more cameras are coupled to a motor for moving the one or more cameras.

10. The method of claim 1, further comprising using the one or more cameras to monitor the patient during the medical process.

11. The method of claim 1, further comprising recording images generated by the one or more cameras.

12. The method of claim 1, further comprising using at least one of the one or more cameras or another camera(s)

to obtain one or more images during the medical process, and processing the one or more images to monitor the patient during the medical process.

13. The method of claim 12, further comprising storing the images in a non-transitory medium.

14. The method of claim 1, further comprising using at least one of the one or more cameras or another camera(s) to obtain one or more images during the medical process, and processing the one or more images to track the object and an additional object during the medical process.

15. The method of claim 14, wherein the additional object comprises the patient, and wherein the object comprises an imaging system, a patient support system, a machine accessory, an immobilization device, or a patient-specific device.

16. The method of claim 1, further comprising using at least one of the one or more cameras or another camera(s) to obtain one or more images during the medical process, and processing the one or more images to determine a spatial distance between the object and another object, an object-to-isocenter distance, a body shape and/or size of the patient, a source-to-skin distance, or a combination of the foregoing.

17. The method of claim 1, wherein the medical process comprises an imaging process, a treatment planning process, a simulation process, or a treatment delivery process.

18. The method of claim 1, wherein the object comprises a patient support, and the information obtained using the one or more cameras is regarding a three dimensional configuration of the patient support.

19. The method of claim 1, wherein the degrees of freedom of the machine part and/or the predetermined trajectory of the machine part are stored as a part of an operation plan.

20. A system for monitoring an object during a medical process, comprising:
one or more cameras, wherein at least one of the cameras comprises multiple sensors configured to sense multiple respective distances from respective points on a surface, and wherein the sensors are identical to each other;
a non-transitory medium storing a three-dimensional model of an object and a movement model of the object, the object being a part of a medical system, the medical system having an energy source configured to deliver energy towards a patient from a distance, wherein the movement model of the object indicates degrees of freedom of a machine component and/or a predetermined trajectory of the machine component; and
a processing unit configured to process images from the one or more cameras to obtain information regarding an actual three-dimensional configuration of the object, the three-dimensional model, and the movement model to monitor the object during the medical process, wherein the three-dimensional model of the object is created without using the one or more cameras;
wherein the processing unit is configured to determine an expected three-dimensional extent of the object for an expected position and an expected orientation of the object, wherein the processing unit is configured to determine the expected three-dimensional extent of the object using the three-dimensional model and the movement model of the object.

21. The system of claim 20, wherein the one or more cameras comprise a depth sensing camera.

22. The system of claim 20, wherein the one or more cameras comprise a plurality of cameras, and the information comprises a three-dimensional rendering of the object obtained using images from the cameras.

23. The system of claim 20, wherein the processing unit is configured to compare the expected three-dimensional configuration of the object with a three-dimensional rendering of the object obtained using images from the one or more cameras.

24. The system of claim 20, wherein the medical system comprises a treatment machine, an imaging device, or a radiation machine.

25. The system of claim 20, wherein the processing unit is configured to monitor the object to determine if there is a possible collision between the object and the patient, or between the object and another object.

26. The system of claim 20, wherein the one or more cameras comprises a camera coupled to a linear accelerator, a radiation treatment machine, a radiation imaging device, or a patient support system.

27. The system of claim 20, wherein the one or more cameras comprises a plurality of cameras coupled to a linear accelerator, a radiation treatment machine, a radiation imaging device, a patient support system, or a combination of the foregoing.

28. The system of claim 20, wherein at least one of the one or more cameras is coupled to a motor and is moveable by the motor.

29. The system of claim 20, wherein the processing unit is configured to use the one or more cameras to monitor the patient during the medical process.

30. The system of claim 20, further comprising a database for storing images generated by the one or more cameras.

31. The system of claim 20, wherein the processing unit is further configured to process one or more images to monitor the patient during the medical process.

32. The system of claim 31, further comprising a non-transitory medium for storing the images.

33. The system of claim 20, wherein the processing unit is further configured to process one or more images to track the object and an additional object during the medical process.

34. The system of claim 33, wherein the additional object comprises the patient, and wherein the object comprises an imaging system, a patient support system, a machine accessory, an immobilization device, and a patient-specific device.

35. The system of claim 20, wherein the processing unit is further configured to process one or more images to determine a spatial distance between the object and another object, an object-to-isocenter distance, a body shape and/or size of the patient, a source-to-skin distance, or any combination of the foregoing.

36. The system of claim 20, wherein the medical process comprises an imaging process, a treatment planning process, a simulation process, or a treatment delivery process.

37. The system of claim 20, wherein the degrees of freedom of the machine part and/or the predetermined trajectory of the machine part are stored as a part of an operation plan.

38. A computer product having a non-transitory medium storing a set of instructions, an execution of which causes a method of monitoring an object during a medical process to be performed, the method comprising:
obtaining information regarding a three dimensional object involved in a medical process using one or more cameras, the object being a part of a medical system, the medical system having an energy source configured to deliver energy towards a patient from a distance;

obtaining a three-dimensional model of the object, wherein the three-dimensional model of the object is created without using the one or more cameras;

obtaining a movement model of the object, wherein the movement model of the object indicates degrees of freedom of a machine component and/or a predetermined trajectory of the machine component; and processing the information, the three-dimensional model, and the movement model to monitor the object during the medical process;

wherein at least one of the cameras comprises multiple sensors configured to sense multiple respective distances from respective points on a surface, and wherein the sensors are identical to each other; and wherein the act of processing comprises determining an expected three-dimensional extent of the object for an expected position and an expected orientation of the object, and wherein the expected three-dimensional extent of the object is determined using the three-dimensional model and the movement model of the object.

39. The computer produce of claim 38, wherein the degrees of freedom of the machine part and/or the predetermined trajectory of the machine part are stored as a part of an operation plan.

* * * * *